US012636034B2

(12) United States Patent (10) Patent No.: US 12,636,034 B2
Nishio (45) Date of Patent: May 26, 2026

(54) MEDICAL DEVICE

(71) Applicant: TERUMO KABUSHIKI KAISHA, Tokyo (JP)

(72) Inventor: Kosuke Nishio, Irvine, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 974 days.

(21) Appl. No.: 17/873,747

(22) Filed: Jul. 26, 2022

(65) Prior Publication Data

US 2022/0361912 A1 Nov. 17, 2022

Related U.S. Application Data

(63) Continuation of application No. PCT/JP2020/014686, filed on Mar. 30, 2020.

(51) Int. Cl.
A61B 17/3207 (2006.01)
(52) U.S. Cl.
CPC *A61B 17/320758* (2013.01); *A61B 2217/005* (2013.01)
(58) Field of Classification Search
CPC ............................................. A61B 17/320758
See application file for complete search history.

(56) References Cited

U.S. PATENT DOCUMENTS 4,917,085 A * 4/1990 Smith ............ A61B 17/320758
606/159
5,041,082 A * 8/1991 Shiber ........................ F16D 7/02
606/159

(Continued)

FOREIGN PATENT DOCUMENTS

JP 2001522631 A 11/2001
JP 2004514463 A 5/2004
(Continued)

OTHER PUBLICATIONS

English Translations of the International Search Report (Form PCT/ISA/210) and the Written Opinion of the International Searching Authority (Form PCT/ISA/237) issued Jun. 30, 2020, by the Japan Patent Office in corresponding International Application No. PCT/JP2020/014686. (12 pages).

(Continued)

*Primary Examiner* — Erin McGrath
(74) *Attorney, Agent, or Firm* — Buchanan Ingersoll & Rooney PC

(57) ABSTRACT

A medical device that reduces stress concentration on a part of a drive shaft and has stable rotation and durability. The medical device that removes an object in a body lumen includes: a rotatable drive shaft; a driving portion configured to apply torque to a proximal portion of the drive shaft and having a specified rated rotation direction; a cutting portion fixed to a distal portion of the drive shaft and configured to cut the object; an outer tubular shaft rotatably accommodating the drive shaft, in which the drive shaft includes a proximal coil and a distal coil disposed on a distal side with respect to the proximal coil, and the distal coil is more deformable in a radial direction than the proximal coil by receiving load torque while the drive shaft is rotating in the rated rotation direction.

19 Claims, 10 Drawing Sheets

(56) References Cited

U.S. PATENT DOCUMENTS

| | | | | |
|---|---|---|---|---|
| 5,108,411 A | * | 4/1992 | McKenzie | A61B 8/445 606/159 |
| 5,816,923 A | * | 10/1998 | Milo | A61B 17/320758 464/902 |
| 6,156,046 A | | 12/2000 | Passafaro et al. | |
| 6,565,588 B1 | | 5/2003 | Clement et al. | |
| 2002/0007190 A1 | | 1/2002 | Wulfman et al. | |
| 2003/0139689 A1 | | 7/2003 | Shturman et al. | |
| 2005/0119615 A1 | | 6/2005 | Noriega et al. | |

FOREIGN PATENT DOCUMENTS

| | | |
|---|---|---|
| JP | 2008521503 A | 6/2008 |
| JP | 2020018710 A | 2/2020 |
| WO | 0176680 A1 | 10/2001 |

OTHER PUBLICATIONS

International Search Report (PCT/ISA/210) with translation and Written Opinion (PCT/ISA/237) mailed on Jun. 30, 2020, by the Japan Patent Office as the International Searching Authority for International Application No. PCT/JP2020/014686. (17 pages).

* cited by examiner

MEDICAL DEVICE

CROSS-REFERENCES TO RELATED APPLICATIONS

This application is a continuation of International Application No. PCT/JP2020/014686 filed on Mar. 30, 2020, the entire content of which is incorporated herein by reference.

TECHNOLOGICAL FIELD

This disclosure generally relates to a medical device for removing an object in a body lumen.

BACKGROUND DISCUSSION

Examples of a treatment method for a stenosed site caused by a plaque, a thrombus, and the like in a blood vessel include a method for dilating the blood vessel by using a balloon, and a method for indwelling a mesh-shaped or coil-shaped stent into the blood vessel as a support for the blood vessel. However, it is difficult for these methods to treat a stenosed site that is hardened by calcification or a stenosed site that is formed at a bifurcated portion in the blood vessel. An atherectomy device is known as a device that can perform treatment in such a case (for example, see U.S. Pat. No. 6,565,588).

The atherectomy device is a device that removes the plaque in the blood vessel by shearing/breaking the plaque by a cutting portion that rotates at a relatively high speed. The atherectomy device includes the cutting portion disposed at a distal end of a catheter, a drive shaft that transmits the high-speed rotation of the cutting portion from outside a body, and a tubular body that rotatably accommodates the drive shaft.

Incidentally, the drive shaft of the atherectomy device is required to have stability during the high-speed rotation and sufficient durability against load torque when the plaque and the like is cut. The drive shaft may be formed using only a single-layer coil. When the single-layer coil is instantaneously subjected to strong load torque, the single-layer coil can rather easily be deformed inside the tubular body. For example, a stress is concentrated on a connection portion between a power supply portion that transmits torque to the drive shaft and the drive shaft, which may cause breakage.

SUMMARY

A medical device is disclosed that reduces stress concentration on a part of a drive shaft and has stable rotation and durability.

One aspect of a medical device according to this disclosure is a medical device that removes an object in a body lumen. The medical device includes: a rotatable drive shaft; a driving portion configured to apply torque to a proximal portion of the drive shaft and having a specified rated rotation direction; a cutting portion fixed to a distal portion of the drive shaft and configured to cut the object; and an outer tubular shaft configured to rotatably accommodate the drive shaft, in which the drive shaft includes a proximal coil and a distal coil disposed on a distal side with respect to the proximal coil, and the distal coil is more deformable in a radial direction than the proximal coil by receiving load torque while the drive shaft is rotating in the rated rotation direction.

Another aspect of the medical device according to this disclosure is a medical device that removes an object in a body lumen. The medical device includes: a rotatable drive shaft; a driving portion configured to apply torque to a proximal portion of the drive shaft; a cutting portion fixed to a distal portion of the drive shaft and configured to cut the object; and an outer tubular shaft configured to rotatably accommodate the drive shaft, in which the outer tubular shaft includes a tubular inner layer and a tubular outer layer surrounding the inner layer, and the inner layer includes a braided wire braided in a tubular shape or a coil wire wound in a spiral shape.

Still another aspect of the medical device according to this disclosure is a medical device that removes an object in a body lumen. The medical device includes: a rotatable drive shaft including at least one coil; a driving portion configured to apply torque to a proximal portion of the drive shaft and having a specified rated rotation direction; a cutting portion fixed to a distal portion of the drive shaft and configured to cut the object; and an outer tubular shaft configured to rotatably accommodate the drive shaft, in which the drive shaft includes, at the proximal portion of the drive shaft, a protection tube covering the coil, and the protection tube is disposed at a position that is on a proximal side with respect to the outer tubular shaft in a direction along an axial center of the drive shaft and overlaps with at least a part of a lumen having an inner diameter larger than an inner diameter of the outer tubular shaft, or at a position that overlaps with at least a part of a hole that penetrates in a direction perpendicular to the axial center of the drive shaft.

In the one aspect of the medical device configured as described above, when excessive load torque is applied to the drive shaft rotating in the rated rotation direction, the distal coil easily comes into contact with an inner peripheral surface of the outer tubular shaft before the proximal coil to generate braking torque. Therefore, a long distance from a portion of the drive shaft that receives the torque from the driving portion to a position at which the braking torque is generated can be secured. Therefore, the medical device reduces stress concentration on a part of the drive shaft and has stable rotation and durability.

In the another aspect of the medical device configured as described above, the inner layer of the outer tubular shaft disposed outside the drive shaft is less likely to be deformed, and the inner diameter is easily maintained substantially constant even when the inner layer is bent. Therefore, it is rather easy to set, to a desirable position, a position at which the braking torque is generated in the drive shaft by contact between the drive shaft and the inner peripheral surface of the outer tubular shaft.

In the still another aspect of the medical device configured as described above, the protective tube can help prevent the coil of the drive shaft disposed at the position overlapping the lumen or the hole from being deformed by receiving the load torque and entering the lumen or the hole wider than the inner diameter of the outer tubular shaft. Therefore, the medical device helps prevent breakage of the drive shaft and has stable rotation and durability.

BRIEF DESCRIPTION OF THE DRAWINGS

FIGS. 5A and 5B are diagrams showing an outer layer tube in a cross-sectional view and a drive shaft in a plan view, in which FIG. 5A shows a first example and FIG. 5B shows a second example.

FIGS. 7A-7C are schematic views showing a state in which a lesion area is removed by the medical device, in which FIG. 7A shows a state in which cutting is started, FIG. 7B shows a state in which the cutting is performed by rotating an outer tubular shaft, and FIG. 7C shows a state in which the cutting is performed while the outer tubular shaft is moved.

FIGS. 8A and 8B illustrate the inner layer in a cross-sectional view and the drive shaft in a plan view, in which FIG. 8A shows a state in which a distal coil is in contact with the inner layer, and FIG. 8B shows a state in which the distal coil and a proximal coil are in contact with the inner layer.

FIGS. 9A and 9B illustrate a first modification, in which FIG. 9A shows a state in which the distal coil is in contact with the inner layer, and FIG. 9B shows a state in which the distal coil and the proximal coil are in contact with the inner layer.

FIGS. 10A and 10B illustrate a second modification, in which FIG. 10A shows a state in which the distal coil is in contact with the inner layer, and FIG. 10B shows a state in which the distal coil and the proximal coil are in contact with the inner layer.

FIGS. 11A and 11B illustrate a third modification, in which FIG. 11A shows a state in which the distal coil is in contact with the inner layer, and FIG. 11B shows a state in which the distal coil and the proximal coil are in contact with the inner layer.

FIGS. 12A and 12B illustrate a fourth modification, in which FIG. 12A shows a state in which the distal coil is in contact with the inner layer, and FIG. 12B shows a state in which the distal coil and the proximal coil are in contact with the inner layer.

FIGS. 13A and 13B illustrate a fifth modification, in which FIG. 13A shows a state in which the distal coil is in contact with the inner layer, and FIG. 13B shows a state in which the distal coil and the proximal coil are in contact with the inner layer.

DETAILED DESCRIPTION

Figure 1:
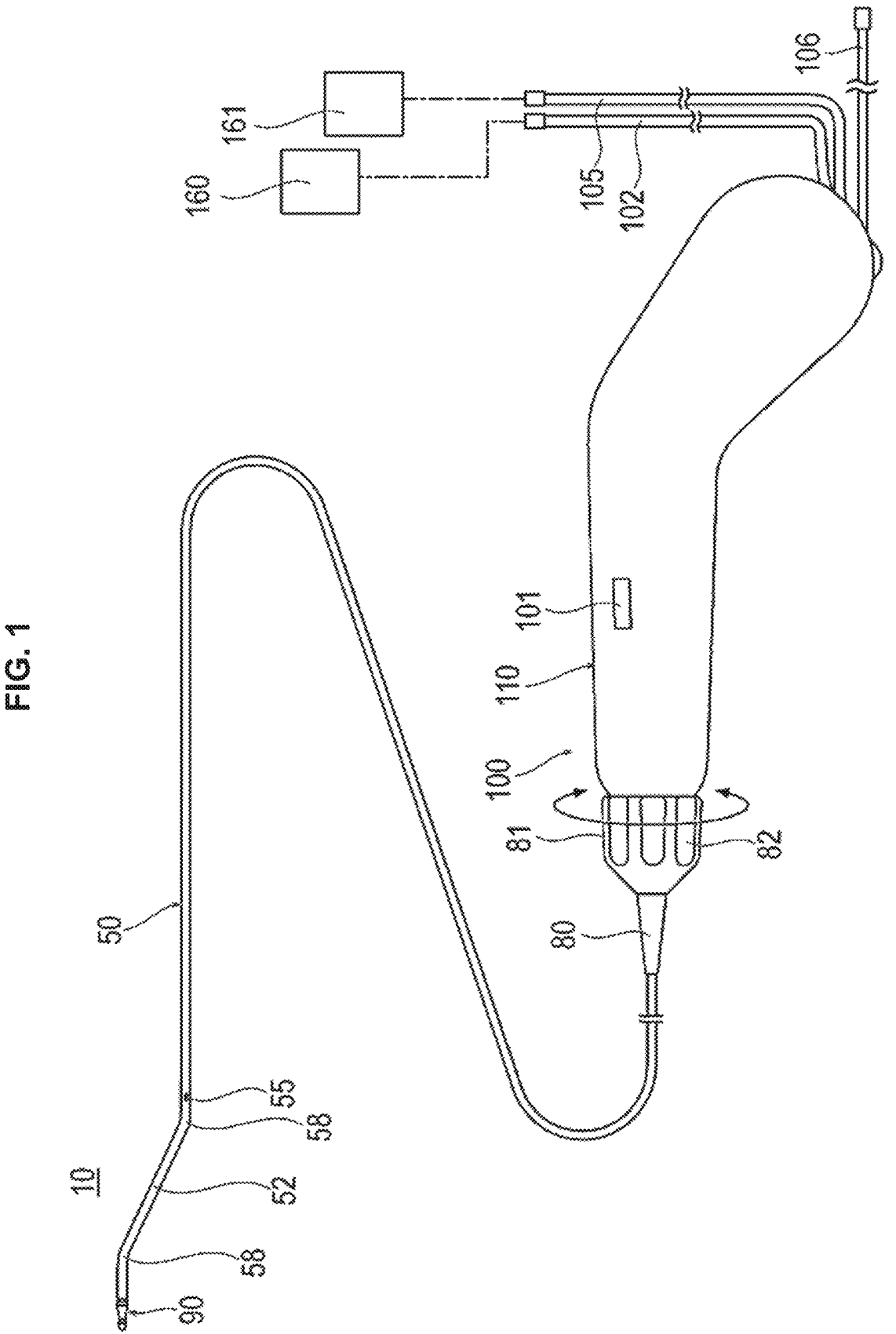
FIG. 1 is a plan view showing a medical device according to an embodiment.

Set forth below with reference to the accompanying drawings is a detailed description of embodiments of a medical device for removing an object in a body lumen. Note that since embodiments described below are preferred specific examples of the present disclosure, although various technically preferable limitations are given, the scope of the present disclosure is not limited to the embodiments unless otherwise specified in the following descriptions. It is noted that a size and a ratio of each member in the drawings may be exaggerated for convenience of description and may differ from an actual size and ratio. In addition, in the present disclosure, a side of a medical device 10 to be inserted into a body lumen is referred to as a "distal side", and a side to be operated is referred to as a "proximal side".

The medical device 10 according to the present embodiment can be inserted into a blood vessel in an acute lower limb ischemia or a deep vein thrombosis and used for a procedure for destroying and removing a thrombus, a plaque, an atheroma, and a calcified lesion. It is noted that an object to be removed is not necessarily limited to the thrombus, the plaque, the atheroma, and the calcified lesion, and any object that may be present in a body lumen may be applicable.

As shown in FIG. 1, the medical device 10 includes an elongated drive shaft 20 that is rotationally driven, an outer tubular shaft 50 that accommodates the drive shaft 20, a cutting portion 90 that cuts a thrombus, a guide wire lumen tube 40 that is disposed inside the drive shaft 20, and a handle 100.

As shown in FIGS. 3 to 6, the outer tubular shaft 50 includes an outer layer 51, an inner layer 60, a shaping distal portion 52, an outer sheath 57 that is attached to an outer peripheral surface of the outer layer 51, a distal bearing portion 53 that is disposed on a distal side with respect to the shaping distal portion 52, and a seal holding portion 70 to which proximal portions of the inner layer 60 and the outer layer 51 are fixed.

The drive shaft 20 is an elongated tubular body that transmits a rotational force to the cutting portion 90. The drive shaft 20 is rotatable inside the outer tubular shaft 50. The drive shaft 20 includes a distal coil 21, a proximal coil 22 that is located on a proximal side of the distal coil 21, a conveying coil 23 that generates a conveying force, and a rotating shaft 24 that is rotatably supported by the distal bearing portion 53, which will be described later, of the outer tubular shaft 50. The drive shaft 20 further includes a tubular interlock portion 25 that interlocks the distal coil 21 with the proximal coil 22, a strain relief member 26 that is fixed to the interlock portion 25, a distal protection tube 27 that is disposed on an outer periphery of a distal portion of the drive shaft 20, a proximal protection tube 28 that is disposed on an outer periphery of a proximal portion of the drive shaft 20, and a proximal tube 29 that is disposed on an outer periphery of the drive shaft 20 on the proximal side with respect to the proximal protection tube 28.

Figure 5A:
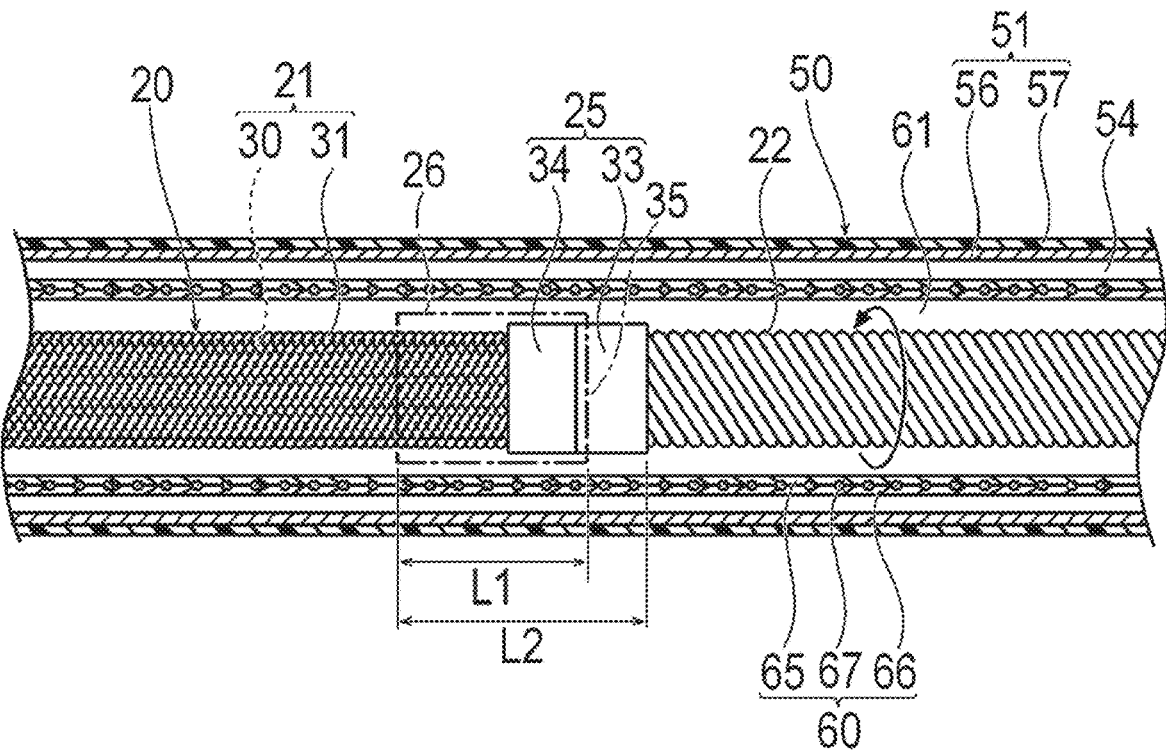

As shown in FIG. 5A, the distal coil 21 can be a multilayer coil in which coils are stacked in layers. The distal coil 21 is more flexible than the proximal coil 22 and has a characteristic that a rotational power applied from the proximal side can be transmitted to the distal side. The distal coil 21 can include a first coil 30 and a second coil 31 surrounding an outer side (outer periphery) of the first coil 30. It is noted that the distal coil 21 may be a multilayer coil having three or more layers (or coils).

When the drive shaft 20 receives torque from the proximal side and receives load torque from the distal side while rotating in a rated rotation direction (a rotation direction of the drive shaft 20 when the medical device 10 is used for cutting and conveyance of the cut object), the first coil 30 is wound in a direction in which a spiral of a wire rod constituting the first coil 30 is loosened and the first coil 30 expands in diameter. That is, the wire rod of the first coil 30 is formed so as to be wound in the rated rotation direction toward the distal side when viewed from the proximal side. The first coil 30 has a characteristic of contracting along an axial center of the first coil 30 while expanding in diameter when the drive shaft 20 receives the load torque while rotating in the rated rotation direction. The first coil 30 may be a single-wire coil in which one wire rod is wound, or may be a multi-wire coil in which a plurality of wire rods are wound side by side.

When the drive shaft 20 receives the torque from the proximal side and receives the load torque from the distal side while rotating in the rated rotation direction, the second coil 31 is wound in a direction in which a spiral of a wire rod constituting the second coil 31 is tightened and the second coil 31 reduces in diameter. That is, the wire rod of the second coil 31 is formed so as to be wound in a direction opposite to the rated rotation direction toward the distal side when viewed from the proximal side. The second coil 31 has a characteristic of extending along an axial center of the second coil 31 while being reduced in diameter when the drive shaft 20 receives the load torque in the rated rotation direction. The second coil 31 may be a single-wire coil in which one wire rod is wound, or may be a multi-wire coil in which a plurality of wire rods are wound side by side.

The second coil 31 is attached to an outer peripheral surface of the first coil 30. Therefore, when the drive shaft 20 rotates in the rated rotation direction and receives the load torque, by contracting the first coil 30 and expanding the first coil 30 in diameter, and extending the second coil 31 and reducing the second coil 31 in diameter, displacement of the first coil 30 and the second coil 31 in a radial direction and an axial direction is cancelled out. Therefore, in the multi-layer coil formed of the first coil 30 and the second coil 31, deformation in the radial direction and the axial direction can be reduced when the drive shaft 20 rotates in the rated rotation direction. It is noted that the second coil 31 has a larger coil radius than the first coil 30, a force of the second coil 31 is stronger than an action of the first coil 30. Therefore, when the drive shaft 20 rotates in the rated rotation direction, the distal coil 21 slightly contracts in the radial direction and slightly expands in the axial direction.

Figure 4:
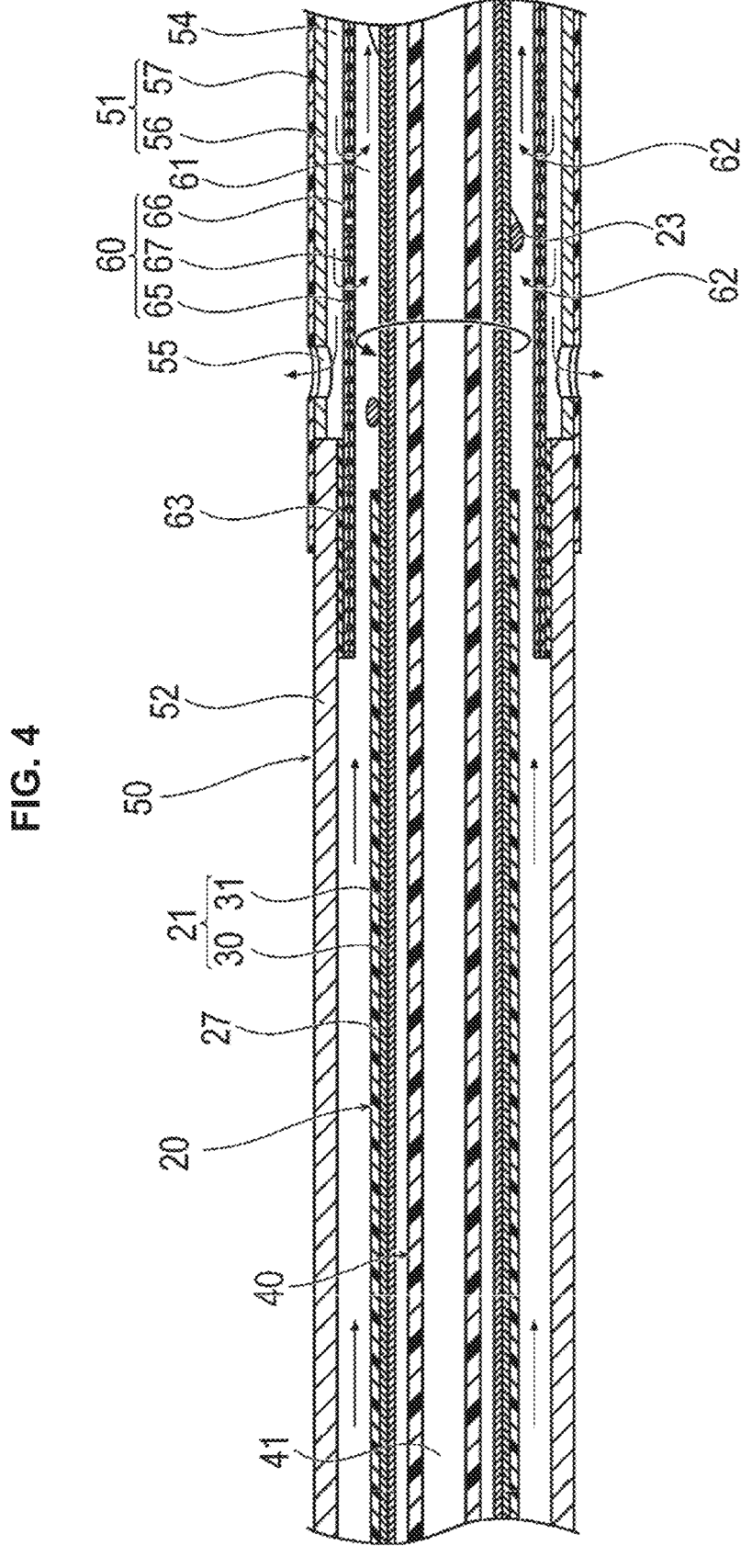
FIG. 4 is a cross-sectional view showing the vicinity of distal portions of an inner layer and an outer layer of the medical device.

As shown in FIG. 4, the conveying coil 23 is attached to an outer peripheral surface of the distal coil 21. The conveying coil 23 is formed by sparsely winding a wire rod constituting the conveying coil 23 with a gap or spacing between windings of the conveying coil 23. The conveying coil 23 functions as an Archimedean screw (screw pump) when the drive shaft 20 rotates in the rated rotation direction, and can convey a liquid or the object in a proximal direction. Therefore, the conveying coil 23 is formed so as to be wound in the rated rotation direction toward the distal side when viewed from the proximal side. A distal end of the conveying coil 23 is located on the proximal side with respect to the bent shaping distal portion 52 disposed at a distal portion of an outer tubular shaft 50. Accordingly, the conveying coil 23 and the bent shaping distal portion 52 can be prevented from being damaged due to friction when the drive shaft 20 rotates. It is noted that the conveying coil 23 may be formed so as to be wound in the direction opposite to the rated rotation direction toward the distal side when viewed from the proximal side. Accordingly, the conveying coil 23 functions as the Archimedean screw (screw pump) when the drive shaft 20 rotates in the rated rotation direction, and conveys the liquid or the object in a distal direction.

Figure 5B:
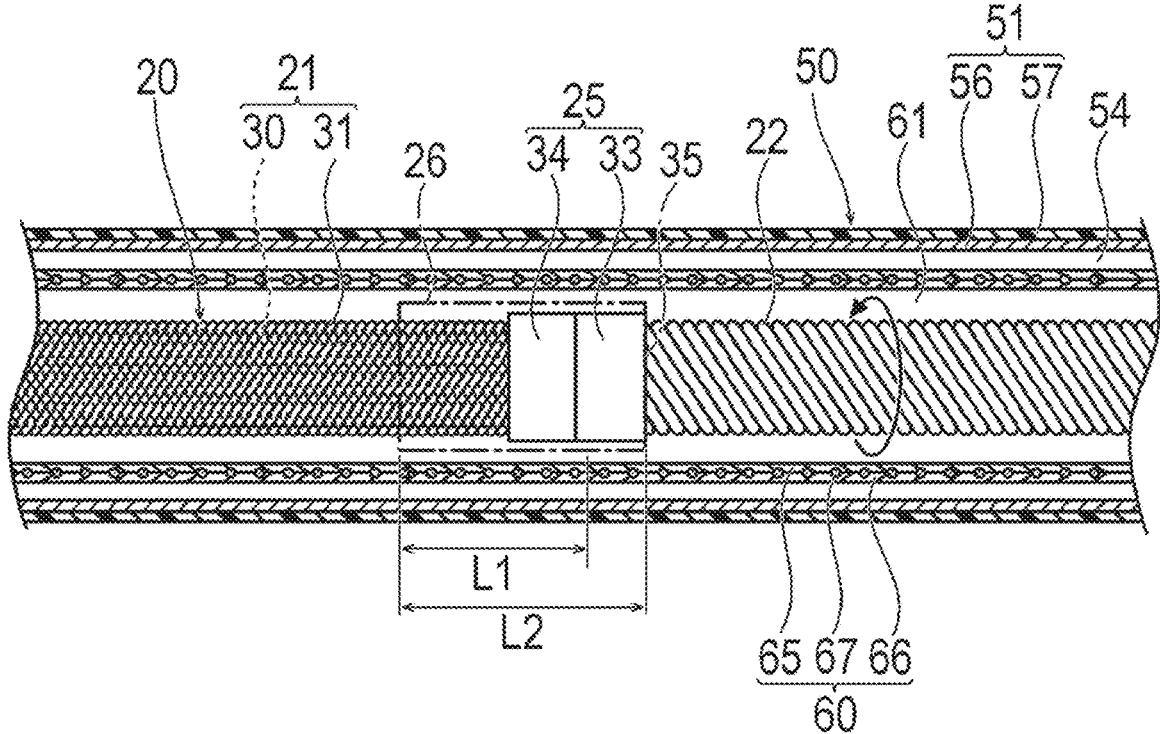

As shown in FIGS. 5A and 5B, the proximal coil 22 can be a single-layer coil formed of only one layer. The proximal coil 22 is flexible and has a characteristic that the rotational power applied from the proximal side can be transmitted to the distal side. When the drive shaft 20 receives the load torque while rotating in the rated rotation direction, the proximal coil 22 is wound in a direction in which a spiral of the proximal coil 22 is loosened and the proximal coil 22 expands in diameter. That is, the proximal coil 22 is formed so as to be wound in the rated rotation direction toward the distal side when viewed from the proximal side. The proximal coil 22 has a characteristic of contracting along an axial center of the proximal coil 22 while expanding in diameter when the drive shaft 20 receives the load torque while rotating in the rated rotation direction. The proximal coil 22 may be a single-wire coil in which one wire rod is wound, or may be a multi-wire coil in which a plurality of wire rods are wound side by side.

An outer diameter and an inner diameter of the distal coil 21 are substantially the same as an outer diameter and an inner diameter of the proximal coil 22. Further, since the distal coil 21 is a multilayer coil and the proximal coil 22 is a single-layer coil, the wire rods of the distal coil 21 are thinner than the wire rod of the proximal coil 22. Therefore, when excessive load torque is applied to the drive shaft 20 rotating in the rated rotation direction, the deformation of the distal coil 21 occurs before the diameter of the proximal coil 22 expands.

The interlock portion 25 includes a tubular distal fixing portion 34 that fixes proximal portions of the wire rods constituting the distal coil 21, and a tubular proximal fixing portion 33 that fixes a distal portion of the wire rod constituting the proximal coil 22. Connection between the wire rods constituting the distal coil 21 and the distal fixing portion 34 and connection between the wire rod constituting the proximal coil 22 and the proximal fixing portion 33 can be performed by, for example, welding using a laser or the like or joining using silver solder (tin-silver solder). The proximal fixing portion 33 and the distal fixing portion 34 can be, for example, in contact with each other side by side in an axial direction of the drive shaft 20, and contact portions of the proximal fixing portion 33 and the distal fixing portion 34 are interlocked by welding using a laser or the like or joining using silver solder (tin-silver solder). An interlock structure of the distal coil 21 and the proximal coil 22 is not particularly limited as long as the distal coil 21 and the proximal coil 22 can be interlocked. For example, the wire rods constituting the distal coil 21 and the wire rod constituting the proximal coil 22 may be directly interlocked by laser welding or the like.

The strain relief member 26 can help prevent breakage of the distal coil 21 at a boundary portion between the flexible distal coil 21 and the rigid interlock portion 25. The strain relief 26 member can be, for example, a rigid circular tube that covers from a position of the proximal fixing portion 33 relatively close to the distal fixing portion 34 to a position on the distal side with respect to a distal end of the distal fixing portion 34. An inner diameter of the strain relief member 26 is slightly larger than the outer diameter of the distal coil 21. Therefore, the distal coil 21 can be bent slightly inside the strain relief member 26, and excessive bending can be prevented. Accordingly, the strain relief member 26 can help prevent the breakage of the distal coil 21. It is noted that the strain relief member 26 may be flexible.

In the absence of the strain relief member 26, when the drive shaft 20 rotates in a bent state in the vicinity of the interlock portion 25, the drive shaft 20 can be strongly rotated in a state in which a strong stress load is applied between the distal coil 21 and the interlock portion 25. The strain relief member 26 helps prevent breakage between distal coil 21 and the interlock portion 25 due to repeated metal fatigue caused by high-speed rotation of the drive shaft 20.

The strain relief member 26 can be joined to the proximal fixing portion 33 at a joint portion 35 located at a proximal end of the strain relief member 26. It is noted that a position of the joint portion 35 is not particularly limited, and may be a proximal portion of the proximal fixing portion 33 as in a second example shown in FIG. 5B. The strain relief member 26 may protrude toward the proximal side with respect to the interlock portion 25 in order to help prevent breakage of the proximal coil 22 at boundary portion between the proximal coil 22 and the interlock portion 25. When the strain relief member 26 is relatively long, a range in which the breakage of the coils can be prevented increases, but the drive shaft 20 is less likely to be bent inside the outer tubular shaft 50. A protruding length L1 of the strain relief member 26 from the interlock portion 25 toward the distal side can be, for example, 1.5 mm. An axial length L2 of a rigid portion formed of the joint portion 35 and the strain relief member 26 can be, for example, 2.5 mm. It is noted that instead of the distal fixing portion 34, the proximal fixing portion 33, and the strain relief member 26, a metal pipe, for example, made of stainless steel or the like, which is laser-cut and has flexibility and rigidity against torque, may be used as the interlock structure of the distal coil 21 and the proximal coil 22. The metal pipe can interlock a proximal surface of the distal coil 21 with a distal surface of the proximal coil 22. In this case, an outer diameter of the metal pipe can be substantially the same as the outer diameters of the distal coil 21 and the proximal coil 22.

As constituent materials for the distal fixing portion 34, the proximal fixing portion 33, and the strain relief member 26 can include, for example, silver solder (tin-silver solder), stainless steel, Ta, Ti, Pt, Au, W, polyolefins such as polyethylene and polypropylene, polyamides, polyesters such as polyethylene terephthalate, fluoropolymers such as an ethylene tetrafluoroethylene copolymer (ETFE), polyether ether ketone (PEEK), and polyimides.

As constituent materials for the distal coil 21, the proximal coil 22, and the conveying coil 23 can include, for example, stainless steel, Ta, Ti, Pt, Au, W, polyolefins such as polyethylene and polypropylene, polyamides, polyesters such as polyethylene terephthalate, fluoropolymers such as an ethylene tetrafluoroethylene copolymer (ETFE), polyether ether ketone (PEEK), and polyimides.

When the drive shaft 20 rotates in the rated rotation direction and receives the load torque, the multilayer distal coil 21 preferably has a diameter such that the multilayer distal coil 21 does not break as a result of twisting, and the diameter of the distal coil 21 is such that the distal coil 21 does not hit the outer tubular shaft 50 so as to be folded back in an axial direction of the outer tubular shaft 50 inside the outer tubular shaft 50 due to twisting. Therefore, an inner diameter of the inner layer 60 of the outer tubular shaft 50 can be, for example, preferably less than 1.75 times the outer diameter of the distal coil 21, and more preferably less than 1.5 times the outer diameter of the distal coil 21.

When the drive shaft 20 rotates in the rated rotation direction and receives the load torque, a deformation amount of the proximal coil 22 of the single layer can be, for example, preferably within a deformation amount by which the proximal coil 22 is not broken due to plastic deformation. Therefore, the inner diameter of the inner layer 60 of the outer tubular shaft 50 can be, for example, preferably less than 1.75 times the outer diameter of the proximal coil 22, and more preferably less than 1.5 times the outer diameter of the proximal coil 22.

When the outer tubular shaft 50 is bent, for example, with a curvature radius of 15 mm, the outermost portion of the distal coil 21 is preferably not in strong contact with an inner peripheral surface of the inner layer 60. In addition, when the guide wire lumen tube 40 is bent, for example, with a curvature radius of 15 mm, the outermost portion of the guide wire lumen tube 40 passing through the inside of the drive shaft 20 is preferably not in strong contact with an inner peripheral surface of the distal coil 21 and an inner peripheral surface of the proximal coil 22.

The rotating shaft 24 is rotatably supported by the distal bearing portion 53 provided on the outer tubular shaft 50. A proximal portion of the rotating shaft 24 can be fixed to the distal coil 21, and a distal portion of the rotating shaft 24 can be fixed to the cutting portion 90. At least one groove-shaped passage 36 extending along an axial center can be, for example, formed in the rotating shaft 24. The passage 36 can allow the object cut by the cutting portion 90 to pass through an inside of the distal bearing portion 53 in the proximal direction.

Figure 3:
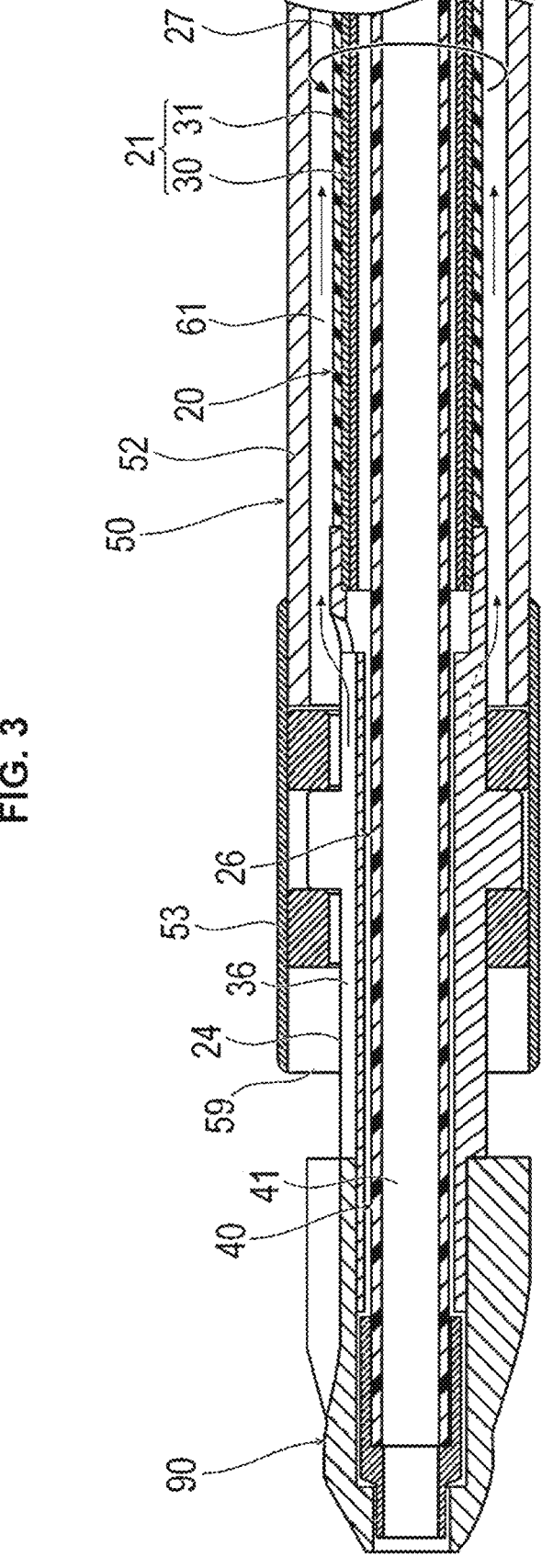
FIG. 3 is a cross-sectional view showing a distal portion of the medical device.

As shown in FIGS. 3 and 4, the distal protection tube 27 is a tubular body that covers the outer peripheral surface of the distal coil 21 on the distal side with respect to the conveying coil 23. The distal protection tube 27 is disposed inside the shaping distal portion 52 provided in the outer tubular shaft 50. The distal protection tube 27 can be formed of, for example, a heat-shrinkable tube whose diameter is reduced by heating and which is in close contact with the distal coil 21. The distal protection tube 27 helps prevent the distal coil 21 and the shaping distal portion 52 from being in contact with each other and being damaged due to the rotation of the drive shaft 20. It is noted that when an inner peripheral surface of the shaping distal portion 52 can be, for example, formed of a resin material instead of a metal material or can be coated with a resin, the distal protection tube 27 may not be provided. In this case, instead of the distal protection tube 27, the conveying coil 23 may be provided in a range in which the distal protection tube 27 is provided.

Figure 6:
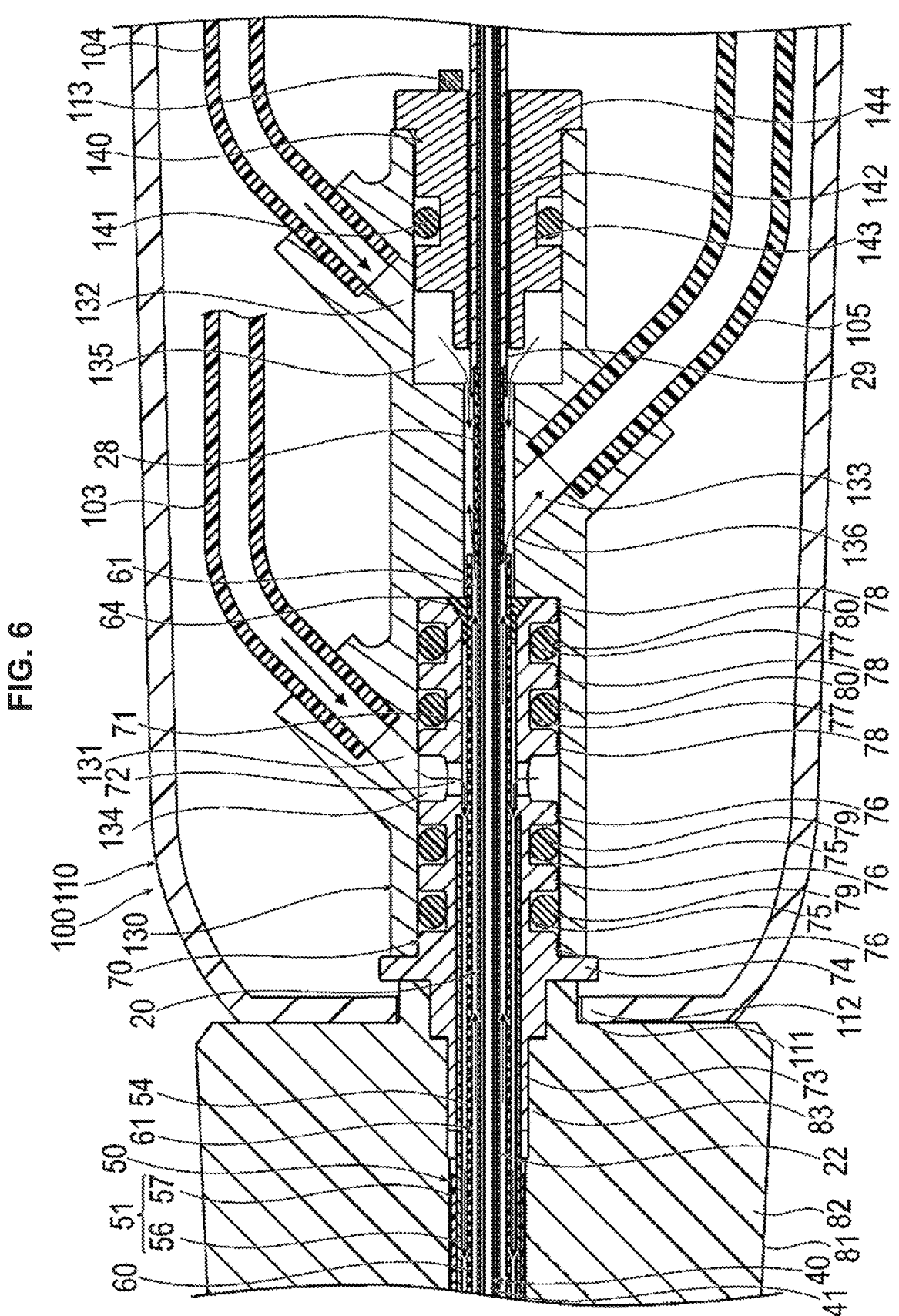
FIG. 6 is a cross-sectional view showing a part of the handle of the medical device.

As shown in FIG. 6, the proximal protection tube 28 can be a tubular body that covers an outer peripheral surface of the proximal coil 22 located in the handle 100. The proximal protection tube 28 can be formed of, for example, a heat-shrinkable tube whose diameter is reduced by heating and which is attached to an outer surface of the proximal coil 22. A distal end of the proximal protection tube 28 is disposed inside the inner layer 60 of the outer tubular shaft 50. A proximal end of the proximal protection tube 28 is disposed inside a power shaft 121. That is, the proximal protection tube 28 covers the proximal coil 22 (drive shaft 20) not surrounded by the outer tubular shaft 50 and the power shaft 121, which is between the outer tubular shaft 50 and the power shaft 121. The proximal coil 22 not surrounded by the outer tubular shaft 50 and the power shaft 121 is surrounded by a discharge lumen 136 having an inner diameter larger than an inner diameter of the outer tubular shaft 50. The discharge lumen 136 communicates with a discharge port 133. For example, the discharge port 133 can be a through-hole. The proximal protection tube 28 can help prevent the proximal coil 22 from expanding in diameter and being in contact with surrounding members (for example, discharge lumen 136 and discharge port 133) due to the rotation of the drive shaft 20, thereby helping prevent the proximal coil 22 and the surrounding members from being damaged.

Constituent materials for the heat-shrinkable tubes are not particularly limited, and the materials for the heat-shrinkable tubes can include, for example, polyolefins, nylon, polyether block amide (PEBAX), polyurethane, or polyethylene terephthalate.

Figure 2:
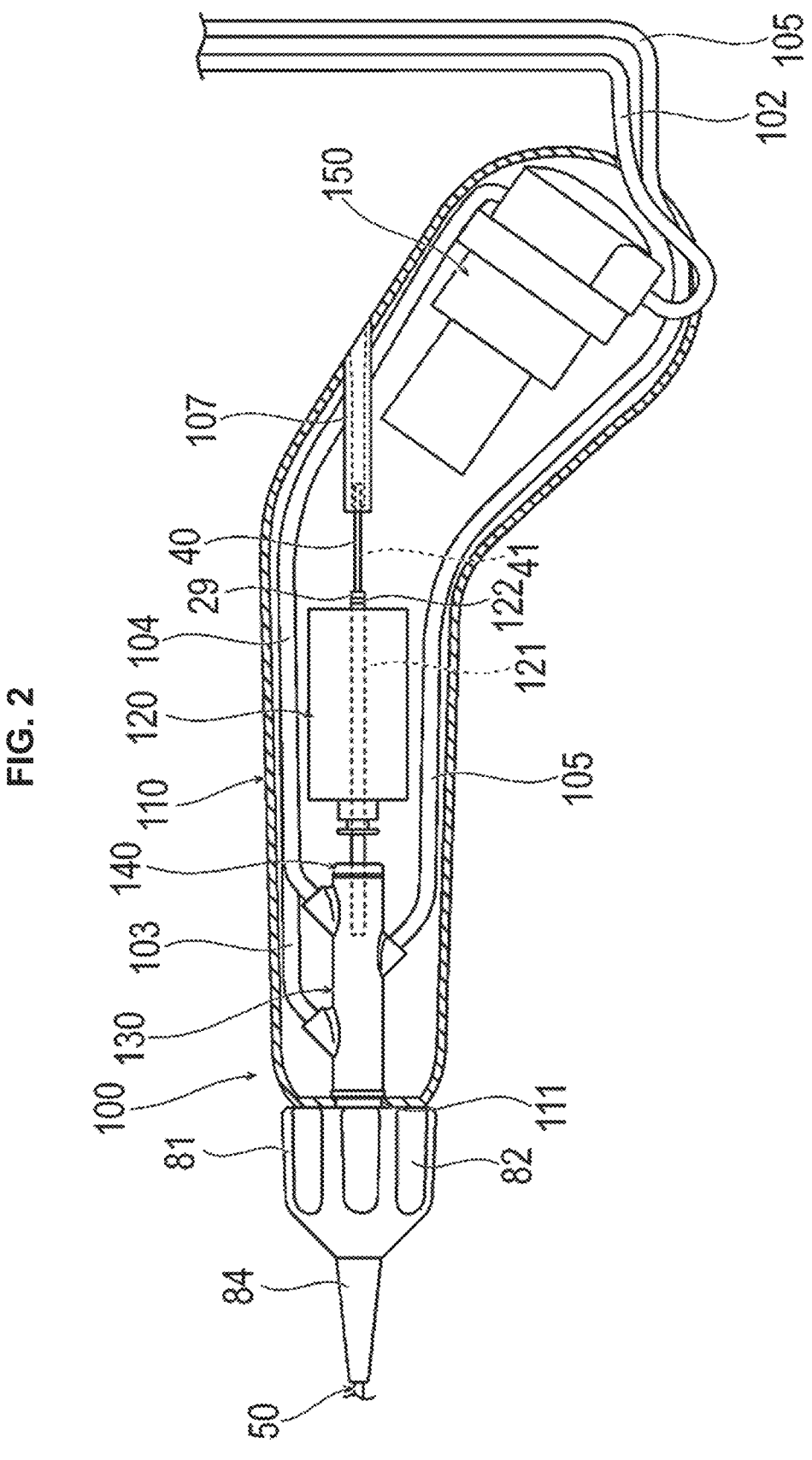
FIG. 2 is a diagram showing a casing of a handle of the medical device in a cross-sectional view, and other parts of the casing of the handle in a plan view.

As shown in FIGS. 3, 4, and 6, the guide wire lumen tube 40 is a tubular body disposed inside the drive shaft 20. A guide wire lumen 41 through which a guide wire passes is formed in the guide wire lumen tube 40. The guide wire passing through the guide wire lumen 41 can be prevented from rubbing against the drive shaft 20. A distal portion of the guide wire lumen tube 40 protrudes toward the distal side with respect to the drive shaft 20, and is disposed inside the cutting portion 90. As shown in FIG. 2, a proximal portion of the guide wire lumen tube 40 is interlocked with a proximal tube 107 that leads out the guide wire, which is disposed in the handle 100.

As shown in FIGS. 3 to 6, the outer tubular shaft 50 is an elongated tubular body that accommodates the drive shaft 20. The outer tubular shaft 50 can transmit, to the distal side, torque that is applied by an operator to an operation portion 81 fixed to a proximal portion of the outer tubular shaft 50. A first lumen 54 for delivering a liquid such as saline (or saline solution) to the distal side can be formed between the outer layer 51 and the inner layer 60. At least one side hole 55 penetrating from an inner peripheral surface to an outer peripheral surface is formed in a distal portion of the outer layer 51. By rotating the outer tubular shaft 50, the cutting portion 90 can be directed to a lesion area.

The proximal portion of the outer layer 51 is fixed to an inner peripheral surface of the seal holding portion 70. The distal portion of the outer layer 51 is fixed to a proximal portion of the shaping distal portion 52. The aforementioned first lumen 54 is formed inside the outer layer 51. The outer layer 51 preferably has flexibility so as to be bent in the body lumen and high torque transmission performance. As a constituent material for the outer layer 51, for example, a circular tube made of a metal material or a resin material having a certain degree of strength, in which spiral slits or grooves are formed by laser processing, can be used. The constituent material for the outer layer 51 is not particularly limited, and can be, for example, a metal material such as stainless steel, nitinol (NiTi), Ta, Ti, Pt, Au, or W, and an engineering plastic such as an ABS resin, polycarbonate (PC), polymethyl methacrylate (PMMA), polyacetal (POM), polyphenyl sulfone (PPSU), polyethylene (PE), a carbon fiber, or polyether ether ketone (PEEK).

The outer sheath 57 is a tubular body that is in relatively close contact with or attached to the outer peripheral surface of the outer layer 51. The outer sheath 57 helps prevent leakage of the liquid in the first lumen 54 from a gap of the spiral slits formed in the outer layer 51. The outer sheath 57 is formed of, for example, a heat-shrinkable tube whose diameter is reduced by heating and which is attached to the outer layer 51.

As shown in FIGS. 4 to 6, the inner layer 60 is disposed inside the outer layer 51 with a gap. The gap between the inner layer 60 and the outer layer 51 is the first lumen 54. A second lumen 61 for discharging the object such as a cut thrombus in the proximal direction is formed inside the inner layer 60. At least one through hole 62 penetrating from an outer peripheral surface to the inner peripheral surface is formed in the inner layer 60. A distal portion of the inner layer 60 is fixed to the inner peripheral surface of the shaping distal portion 52 with a first sealing portion 63 which can be, for example, an adhesive or the like. A proximal portion of the inner layer 60 protrudes toward the proximal side with respect to the outer layer 51, and is fixed to the inner peripheral surface of the seal holding portion 70 with a second sealing portion 64 which can be, for example, an adhesive or the like.

In order to appropriately maintain a gap between the inner layer 60 and the rotatable drive shaft 20 accommodated in the inner layer 60, the inner layer 60 preferably has a structure capable of being flexibly bent and maintaining a cross-sectional shape even when the inner layer 60 is bent. Therefore, the inner layer 60 preferably includes a reinforcement body 67. The inner layer 60 can include a tubular first layer 65 that is disposed in the inner layer 60, a tubular second layer 66 that is disposed in close contact with an outer side of the first layer 65, and the reinforcement body 67 that is disposed between the first layer 65 and the second layer 66. The first layer 65 and the second layer 66 can be, for example, formed of a resin material. The reinforcement body 67 is formed of a braided wire braided in a tubular shape. Alternatively, the reinforcement body 67 may be a spiral coil wire. The reinforcement body 67 in the form of a spiral coil wire can be formed by, for example, winding a wire rod or removing an unnecessary portion of a circular tube by laser processing. A constituent material for the reinforcement body 67 is preferably harder than the first layer 65 and the second layer 66, and for example, a shape memory alloy such as stainless steel, Ta, Ti, Pt, Au, W, or Ni—Ti can be used for the reinforcement body 67.

The resin material forming the inner layer 60 preferably has a certain degree of flexibility and low friction, and polyether ether ketone (PEEK), fluoropolymers such as PTFE and ETFE, polymethyl methacrylate (PMMA), polyethylene (PE), a polyether block amide copolymer (PEBAX), nylon, polyimides, or a combination of the resin materials listed can be used as the resin material for the inner layer 60.

As shown in FIGS. 3 and 4, the shaping distal portion 52 is located at a distal portion of the outer tubular shaft 50. The shaping distal portion 52 is bent at two bent portions 58 such that an axial center of the proximal portion and an axial center of a distal portion of the shaping distal portion 52 are shifted from each other. It is noted that the number of bent portions 58 may be one or three or more. By rotating the outer tubular shaft 50, the shaping distal portion 52 can cause the cutting portion 90 to face the lesion area and further strongly press the cutting portion 90 against the lesion area. As a constituent material for the shaping distal portion 52, for example, a material applicable to the aforementioned outer layer 51 can be used.

As shown in FIG. 6, the proximal portion of the outer layer 51 and the proximal portion of the inner layer 60 are fixed to the seal holding portion 70, and at least a part of the seal holding portion 70 is disposed inside a housing 130 provided in the handle 100. The seal holding portion 70 holds a plurality of seals and is rotatably supported inside the housing 130. The seal holding portion 70 includes a holding portion lumen 71 that penetrates along the axial center of the drive shaft 20, a supply hole 72 that penetrates from an outer peripheral surface to the holding portion lumen 71, an operation fixing portion 73 that is fixed to the operation portion 81 to be described later, and a restraining portion 74 that restrains a position of the sealing holding portion 70 in an axial direction. The seal holding portion 70 further includes two first groove portions 75 that are formed on the outer peripheral surface on the distal side with respect to the supply hole 72, three first stoppers 76 that are arranged alternately with the first groove portions 75, two second groove portions 77 that are formed on the outer peripheral surface on the proximal side with respect to the supply hole 72, and three second stoppers 78 that are arranged alternately with the second groove portions 77.

The drive shaft 20 and the guide wire lumen tube 40 pass through the holding portion lumen 71. The outer layer 51 can be fixed to, with an adhesive or the like, a distal side of the holding portion lumen 71 with respect to the supply hole 72. The inner layer 60 that protrudes from a proximal opening portion of the outer layer 51 to the proximal direction inside the outer layer 51 is fixed to, with the second sealing portion 64, a proximal side of the holding portion lumen 71 with respect to the supply hole 72. Therefore, the first lumen 54 between the outer layer 51 and the inner layer 60 communicates with the supply hole 72.

The operation fixing portion 73 protrudes toward the distal side and is fixed to the operation portion 81 operated by the operator, for example, with a finger. The restraining portion 74 includes a surface facing the distal side. The restraining portion 74 is attached to a restraining receiving portion 112 of the handle 100, which will be described later, and is restrained from moving toward the distal side.

Each of the first groove portions 75 accommodates a first seal portion 79, for example, such as an O-ring. The first seal portion 79 maintains liquid-tightness between the seal holding portion 70 and the housing 130 while maintaining a state in which the seal holding portion 70 is rotatable inside the housing 130. The first stopper 76 helps prevent the first seal portion 79 from separating from the first groove portion 75. Each of the second groove portions 77 can accommodate a second seal portion 80, for example, such as an O-ring. The second seal portion 80 maintains the liquid-tightness between the seal holding portion 70 and the housing 130 while maintaining the state in which the seal holding portion 70 is rotatable inside the housing 130. The second stopper 78 helps prevent the second seal portion 80 from separating from the second groove portion 77.

As shown in FIGS. 1 and 2, the operation portion 81 and an anti-kink protector 84 are fixed to an outer peripheral surface of the proximal portion of the outer tubular shaft 50. The anti-kink protector 84 helps prevent a kink at the proximal portion of the outer tubular shaft 50. An outer surface of the operation portion 81 may be formed with irregularities so as to be rather easily caught by the operator, for example, with the finger.

As shown in FIG. 3, the distal bearing portion 53 is disposed at the distal portion of the outer tubular shaft 50, and rotatably supports the rotating shaft 24 provided on the drive shaft 20. The distal bearing portion 53 is fixed to the distal portion of the shaping distal portion 52. The distal bearing portion 53 can be formed with, on a distal side of the distal bearing portion 53, a distal opening portion 59 through which the object such as a cut thrombus, blood, and the liquid discharged from the side hole 55 are conveyed and taken into the second lumen 61. A distal end of the distal bearing portion 53 is located on a proximal side of the cutting portion 90.

The cutting portion 90 is a member that cuts and reduces the object such as a thrombus, a plaque, or a calcified lesion. Therefore, the "cut" means applying a force to the object in contact to make the object smaller. A method for applying the force in the cutting and a shape or a form of the object after the cutting are not limited. The cutting portion 90 has strength to cut the above-described object. The cutting portion 90 is fixed to an outer peripheral surface of the distal portion of the drive shaft 20. The cutting portion 90 can have a large number of minute abrasive grains on a surface of the cutting portion 90. Alternatively, the cutting portion 90 may include a sharp blade.

A constituent material for the cutting portion 90 preferably has sufficient strength to cut a thrombus, and for example, stainless steel, Ta, Ti, Pt, Au, W, a shape memory alloy, and a cemented carbide can be used for the cutting portion 90.

As shown in FIGS. 1, 2, and 6, the handle 100 is a portion operated by the operator. The handle 100 can include a casing 110, a driving portion 120, the housing 130, a proximal closing portion 140, and a liquid delivering portion 150. The handle 100 further can include a switch 101, a suction tube 102, a first liquid delivering tube 103, a second liquid delivering tube 104, a discharge tube 105, an electric cable 106, and the proximal tube 107.

The casing 110 forms an outline of the handle 100. The casing 110 can accommodate the driving portion 120, the housing 130, the proximal closing portion 140, the first liquid delivering tube 103, the second liquid delivering tube 104, a part of the discharge tube 105, and a part of the electric cable 106. A passage hole 111 through which the drive shaft 20, the outer tubular shaft 50, and the guide wire lumen tube 40 pass is formed in a distal portion of the casing 110. A surface on a proximal side of the passage hole 111 is the restraining receiving portion 112 that is attached to the restraining portion 74 of the seal holding portion 70 and restricts movement of the seal holding portion 70 in the distal direction. The proximal tube 107 is interlocked with the proximal portion of the guide wire lumen tube 40. The proximal tube 107 has a lumen that communicates with the guide wire lumen 41, and guides the guide wire to the proximal side.

The driving portion 120 can be, for example, a hollow motor. The driving portion 120 includes the hollow power shaft 121 that is rotated by electric power supplied from an outside via the electric cable 106. The power shaft 121 passes through the driving portion 120 and rotates while being supported by a bearing. The drive shaft 20 can be accommodated in the power shaft 121. An inner peripheral surface of the power shaft 121 is in slidable contact with an outer peripheral surface of the drive shaft 20. The drive shaft 20 substantially penetrates the power shaft 121, and can be fixed to, by welding, bonding, or the like, a shaft joint portion 122 of a proximal portion of the power shaft 121 at the proximal portion of the drive shaft 20. A rotation speed of the power shaft 121 is not particularly limited, and the rotation speed of the power shaft 121 can be, for example, 5,000 rpm (revolutions per minute) to 200,000 rpm. The driving portion 120 is connected to a control apparatus and can be controlled from an inside or an outside of the handle 100.

The electric cable 106 can be connected to an external power supply or the control apparatus. The switch 101 is a portion operated by the operator to drive and stop the driving portion 120. The switch 101 can be located on an outer surface of the casing 110. It is noted that when a battery is provided in the handle 100, the electric cable 106 is located in the handle 100 and connected to the battery. When the electric cable 106 is connected to the external power supply, the control apparatus can be provided in the handle 100 to perform signal processing on an operation input of the switch 101 and control the driving portion 120 and the liquid delivering portion 150.

The operation portion 81 is a portion that is operated by the operator with the finger to apply rotational torque to the outer tubular shaft 50. The operation portion 81 is fixed to the operation fixing portion 73 of the seal holding portion 70. The operation portion 81 can include an operation rotating body 82 and a fixing recessed portion 83. The operation rotating body 82 can be, for example, a substantially disk-shaped portion operated by the operator with the finger. An outer peripheral surface of the operation rotating body 82 can have relatively high frictional resistance so as to be rather easily operated. The operation fixing portion 73 of the seal holding portion 70 is fitted into the fixing recessed portion 83 so as to be fixed. When the operator rotates the operation portion 81, the outer tubular shaft 50 fixed to the operation portion 81 rotates with respect to the drive shaft 20, the guide wire lumen tube 40, and the casing 110. At this time, the first seal portion 79 and the second seal portion 80 held by the seal holding portion 70 to which the operation portion 81 is fixed slide on an outer peripheral surface of the seal holding portion 70 while receiving frictional resistance. The frictional resistance of the first seal portion 79 and the second seal portion 80 with respect to the seal holding portion 70 is large enough to hold an orientation of a rotation direction of the outer tubular shaft 50. Therefore, when the operator releases the finger after operating the operation rotating body 82 and rotating the outer tubular shaft 50, a rotated position of the outer tubular shaft 50 is held by the frictional resistance of the first seal portion 79 and the second seal portion 80 with respect to the seal holding portion 70. It is noted that the first seal portion 79 and the second seal portion 80 may be held by the inner peripheral surface of the seal holding portion 70 and can slide on an inner peripheral surface of the housing 130.

The housing 130 can include a first liquid delivering port 131 and a second liquid delivering port 132 through which the liquid is delivered, and the discharge port 133 through which the liquid or the object is discharged. The housing 130 can further include a first liquid delivering lumen 134 with which the first liquid delivering port 131 communicates, a second liquid delivering lumen 135 with which the second liquid delivering port 132 communicates, and the discharge lumen 136 with which the discharge port 133 communicates.

The first liquid delivering lumen 134 can have a predetermined inner diameter and is disposed at a distal portion of the housing 130. The first liquid delivering lumen 134 rotatably accommodates the seal holding portion 70. The first seal portion 79 and the second seal portion 80 held by the seal holding portion 70 are in slidable contact with an inner peripheral surface of the first liquid delivering lumen 134. The first liquid delivering port 131 is disposed at a position where the first liquid delivering port 131 communicates with the supply hole 72 of the seal holding portion 70. The first liquid delivering port 131 is located on the proximal side with respect to the first seal portion 79 and on the distal side with respect to the second seal portion 80. The first liquid delivering port 131 is connected to the first liquid delivering tube 103 and can receive the liquid from the first liquid delivering tube 103. The liquid delivered to the first liquid delivering port 131 can flow into the first lumen 54 formed between the outer layer 51 and the inner layer 60 of the outer tubular shaft 50 from the supply hole 72 of the seal holding portion 70. At this time, the first seal portion 79 helps prevent the liquid in the first liquid delivering lumen 134 from leaking to an outside of the housing 130. In addition, the second seal portion 80 helps prevent the liquid in the first liquid delivering lumen 134 from leaking to the discharge lumen 136. In addition, the second sealing portion 64 that fixes the inner layer 60 and the seal holding portion 70 helps prevent the liquid flowing into the first lumen 54 from leaking to the discharge lumen 136 on the proximal side. It is noted that the first seal portion 79 and the second seal portion 80 may be disposed in a groove formed in the inner peripheral surface of the first liquid delivering lumen 134 instead of the seal holding portion 70.

The second liquid delivering lumen 135 has a predetermined inner diameter and is disposed at a proximal portion of the housing 130. The second liquid delivering lumen 135 is disposed on the proximal side with respect to the first liquid delivering lumen 134 and on the proximal side with respect to the discharge lumen 136. The second liquid delivering lumen 135 accommodates a part of the proximal closing portion 140 that seals the second liquid delivering lumen 135. The third seal portion 141 held by the proximal closing portion 140 is in contact with an inner peripheral surface of the second liquid delivering lumen 135. A position of the second liquid delivering lumen 135 which is in contact with the third seal portion 141 is on the proximal side with respect to the second liquid delivering port 132. A distal side of the second liquid delivering lumen 135 communicates with the discharge lumen 136. The second liquid delivering port 132 is connected to the second liquid delivering tube 104 and can receive the liquid from the second liquid delivering tube 104. The liquid delivered to the second liquid delivering port 132 can flow into the discharge lumen 136 communicating with the second liquid delivering lumen 135. At this time, the third seal portion 141 helps prevent the liquid in the second liquid delivering lumen 135 from leaking to the outside of the housing 130.

The discharge lumen 136 is disposed on a proximal side of the first liquid delivering lumen 134 and on the distal side of the second liquid delivering lumen 135. The discharge lumen 136 is formed continuously with the first liquid delivering lumen 134 and the second liquid delivering lumen 135. An inner diameter of the discharge lumen 136 is smaller than the inner diameter of the first liquid delivering lumen 134 and the inner diameter of the second liquid delivering lumen 135. The discharge port 133 is connected to the discharge tube 105. A proximal end of the outer tubular shaft 50 is open in the discharge lumen 136. The drive shaft 20 protruding from the proximal end of the outer tubular shaft 50 to the proximal direction passes through the discharge lumen 136 and further extends in the proximal direction. Therefore, the second lumen 61 formed between the outer tubular shaft 50 and the drive shaft 20 communicates with the discharge lumen 136. The discharge lumen 136 can receive the liquid or the object from the second lumen 61 and discharge the liquid or the object from the discharge port 133 to the discharge tube 105.

The proximal closing portion 140 can be a member that is inserted into the second liquid delivering lumen 135 from a proximal side of the housing 130 and closes the second liquid delivering lumen 135. The proximal closing portion 140 includes a closing portion lumen 142 penetrating along the axial center of the drive shaft 20, a third groove portion 143 formed in an outer peripheral surface of the proximal closing portion 140, and a lid portion 144 attached to a proximal surface of the housing 130. The drive shaft 20, the power shaft 121, and the guide wire lumen tube 40 pass through the closing portion lumen 142.

The third groove portion 143 accommodates the third seal portion 141, for example, such as an O-ring. The third seal portion 141 is in contact with the proximal closing portion 140 and the second liquid delivering lumen 135, and maintains liquid-tightness between the proximal closing portion 140 and the second liquid delivering lumen 135.

A distal surface of the lid portion 144 is attached to the proximal surface of the housing 130. A proximal surface of the lid portion 144 is supported in contact with a lid support portion 113 protruding from the casing 110. The proximal closing portion 140 is supported by the lid support portion 113 and prevented from coming off from the housing 130.

Constituent materials for the first seal portion 79, the second seal portion 80, and the third seal portion 141 are preferably an elastic body, and examples of the constituent materials for the first seal portion 79, the second seal portion 80, and the third seal portion 141 can include silicone rubber, ethylene propylene rubber, nitrile rubber, chloroprene rubber, isoprene rubber, butyl rubber, styrene butadiene rubber, natural rubber such as polyurethane, synthetic rubber, and a silicone resin. It is noted that a hard resin material such as PTFE, FEP, or nylon may be used as the constituent materials for the first seal portion 79, the second seal portion 80, and the third seal portion 141. As shown in FIG. 6, cross-sectional shapes of the first seal portion 79, the second seal portion 80, and the third seal portion 141 are not limited to a circular or elliptical shape, and may be, for example, a rectangular shape.

As constituent materials for the housing 130, the seal holding portion 70, the lid portion 144, and the operation portion 81, for example, ultra-high molecular weight polyethylene, polyesters, polyamides, fluorine-based resins such as polytetrafluoroethylene, an ABS resin, polyacetal (POM), polycarbonate (PC), polypropylene (PP), polybutylene terephthalate (PBT), polymethyl methacrylate (PMMA), and a combination of two or more of the constituent materials listed above (polymer alloys, polymer blends, laminates, or the like) can be used.

The liquid delivering portion 150 is a pump that delivers the liquid to the housing 130 via a liquid delivering tube. The liquid delivering portion 150 is connected to the suction tube 102 that receives a supply of the liquid, for example, such as saline (saline solution), from a liquid delivering source outside the casing 110, and can suction the liquid from the suction tube 102. The liquid delivering portion 150 is connected to the first liquid delivering tube 103 and the second liquid delivering tube 104, and can discharge the suctioned liquid to the first liquid delivering tube 103 and the second liquid delivering tube 104. The external liquid delivering source can be, for example, a saline bag 160, but is not limited to a saline bag 160. The liquid delivering portion 150 may be provided outside the handle 100 instead of being provided in the handle 100. The liquid delivering portion 150 is not limited to a pump as long as a liquid delivering pressure can be generated, and the liquid delivering portion 150 may be, for example, a syringe, a bag suspended from a drip tower, or a pressurized bag.

The discharge tube 105 is a tube that discharges the liquid or the object to the outside of the casing 110. The discharge tube 105 can be connected to, for example, a waste liquid bag 161 capable of accommodating the liquid or the object. It is noted that the discharge tube 105 may be connected to an aspiration source that can perform active aspiration, such as a pump or a syringe.

It is noted that the proximal portion of the drive shaft 20 is connected to the power shaft 121 via the proximal tube 29 provided on an outer peripheral side of the drive shaft 20. The drive shaft 20 can be welded or bonded at a proximal portion of the proximal tube 29, and the proximal tube 29 is bonded or welded to the power shaft 121, whereby the drive shaft 20 is fixed. When the proximal closing portion 140 and the drive shaft 20 are directly connected to each other, a large amount of leakage occurs due to the rotation of the drive shaft 20 formed with the coils, but the leakage can be reduced by interposing the proximal tube 29 between the proximal closing portion 140 and the drive shaft 20.

Next, a method for using the medical device 10 according to the embodiment will be described. Here, a case where a calcified lesion area in a blood vessel is destroyed and conveyed will be described as an example.

Figures 7A, 7B, 7C:
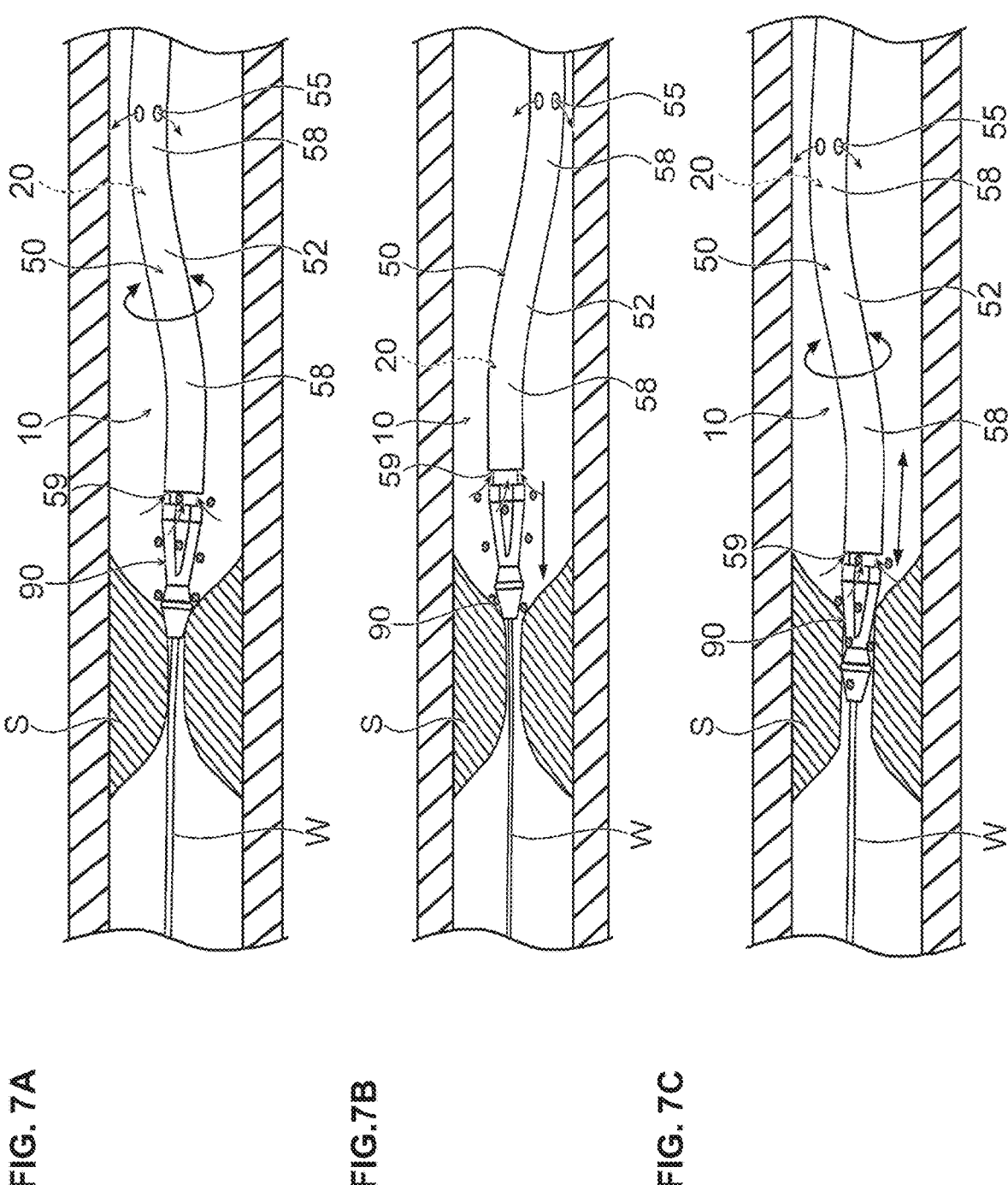

First, the operator inserts a guide wire W into the blood vessel and causes the guide wire W to reach the vicinity of a lesion area S. Next, the operator inserts a proximal end of the guide wire W into the guide wire lumen 41 of the medical device 10. Thereafter, as shown in FIG. 7A, the cutting portion 90 of the medical device 10 is moved to the vicinity of the lesion area S using the guide wire W as a guide.

Next, the operator operates the switch 101 to start operations of the driving portion 120 and the liquid delivering portion 150. Accordingly, the power shaft 121 of the driving portion 120 rotates, and the drive shaft 20 fixed to the power shaft 121 and the cutting portion 90 fixed to the drive shaft 20 rotate. Accordingly, the operator can cut the lesion area S by the cutting portion 90. In addition, when the power shaft 121 rotates, as shown in FIG. 4, the conveying coil 23 disposed on the outer peripheral surface of the drive shaft 20 generates a force for conveying the liquid or the object in the second lumen 61 to the proximal side. Accordingly, as shown in FIG. 3 and FIG. 7A, the conveying force is applied to the distal opening portion 59 of the outer tubular shaft 50.

When the operator wants to change a position of the cutting portion 90 in a circumferential direction, the operator can operate the operation portion 81 shown in FIGS. 1, 2, and 6. When the operator rotates the operation rotating body 82, the outer tubular shaft 50 fixed to the operation portion 81 rotates. As shown in FIG. 6, the seal holding portion 70 of the outer tubular shaft 50 to which the operation portion 81 is fixed rotates inside the first liquid delivering lumen 134 of the housing 130. At this time, the seal holding portion 70 slides on inner peripheral surfaces of the first seal portion 79 and the second seal portion 80. When the outer tubular shaft 50 rotates, as shown in FIG. 7B, a position and a direction of a portion of the outer tubular shaft 50 on the distal side with respect to the bent portions 58 are changed, and the position and a direction of the cutting portion 90 can be changed. Therefore, cutting can be performed while changing the position and the direction of the cutting portion 90 only by operating the operation portion 81 instead of rotating the entire handle 100 that may be difficult to rotate. Further, the operator moves the entire handle 100 or the outer tubular shaft 50 exposed to the outside of the body to reciprocate the outer tubular shaft 50 along a longitudinal direction of the blood vessel. Accordingly, as shown in FIG. 7C, the lesion area S can be cut along the longitudinal direction of the blood vessel by the cutting portion 90.

When the operation of the liquid delivering portion 150 is started, the saline is suctioned into the liquid delivering portion 150 from the suction tube 102 and discharged to the first liquid delivering tube 103 and the second liquid delivering tube 104, as shown in FIGS. 1, 2, and 6. The saline discharged to the first liquid delivering tube 103 flows into the first liquid delivering lumen 134 of the housing 130 from the first liquid delivering port 131. The saline flowing into the first liquid delivering lumen 134 from the first liquid delivering port 131 flows into the first lumen 54 formed between the outer layer 51 and the inner layer 60 from the supply hole 72 of the seal holding portion 70. At this time, the first seal portion 79 helps prevent the saline in the first liquid delivering lumen 134 from leaking to the outside of the housing 130. In addition, the second seal portion 80 helps prevent the saline in the first liquid delivering lumen 134 from leaking to the discharge lumen 136. In addition, the second sealing portion 64 that fixes the inner layer 60 and the seal holding portion 70 helps prevent the saline flowing into the first lumen 54 from leaking to the discharge lumen 136. Therefore, the saline flowing into the first liquid delivering lumen 134 from the first liquid delivering port 131 can be effectively guided to the first lumen 54 while maintaining a relatively high liquid delivering pressure.

The saline discharged to the second liquid delivering tube 104 flows into the second liquid delivering lumen 135 of the housing 130 from the second liquid delivering port 132. The third seal portion 141 helps prevent the saline in the second liquid delivering lumen 135 from leaking to the outside of the housing 130. In addition, the saline supplied from the second liquid delivering tube 104 to the second liquid delivering lumen 135 flows into the discharge lumen 136 on the distal side.

The saline entering the first lumen 54 from the first liquid delivering port 131 via the first liquid delivering lumen 134 moves in the distal direction. As shown in FIGS. 4 and 7A-7C, the saline flowing through the first lumen 54 in the distal direction is released into the blood vessel from the side hole 55 formed in the distal portion of the outer layer 51. In addition, a part of the saline flowing through the first lumen 54 in the distal direction flows into the inner second lumen 61 through the through hole 62. As shown in FIGS. 3 and 7A-7C, a part of the saline discharged into the blood vessel, together with the blood and the cut object, is conveyed to the second lumen 61 from the distal opening portion 59 of the outer tubular shaft 50. The object and the liquid entering the second lumen 61 move in the second lumen 61 in the proximal direction. The object and the blood conveyed to the second lumen 61 are diluted by the saline discharged from the side hole 55 into the blood vessel. Further, as shown in FIG. 4, the object and the liquid conveyed to the second lumen 61 are diluted by the saline directly flowing into the second lumen 61 from the through hole 62. Therefore, viscosity of the discharged material can be reduced to prevent formation of a thrombus in the second lumen 61. Therefore, conveying performance can be improved while preventing a decrease in the conveying force or damage of the medical device 10 due to the formation of the thrombus in the second lumen 61. In addition, the thrombus formed in the medical device 10 can be prevented from flowing into the body lumen. By mixing an anticoagulant, for example, such as heparin into the saline in advance, an effect of preventing the thrombus formation can be improved.

When the liquid or the object entering the second lumen 61 moves in the second lumen 61 in the proximal direction, the liquid or the object reaches the discharge lumen 136 of the housing 130 from a proximal opening portion of the inner layer 60, as shown in FIG. 6. When the liquid or the object reaches the discharge lumen 136, the liquid or the object is discharged from the discharge port 133 to the external waste liquid bag 161 via the discharge tube 105, as shown in FIG. 1.

As shown in FIG. 6, the saline flows into the discharge lumen 136 from the second liquid delivering lumen 135 on the proximal side. Accordingly, the liquid or the object flowing into the discharge lumen 136 from the second lumen 61 can be diluted by the saline. Therefore, the viscosity of the discharged material can be reduced to help prevent formation of thrombi in the second lumen 61, the discharge lumen 136, and the discharge tube 105. Therefore, the conveying performance can be improved while preventing the decrease in the conveying force or the damage of the medical device 10 due to the formation of the thrombi in the second lumen 61, the discharge lumen 136, and the discharge tube 105. In this case, by mixing the anticoagulant such as heparin into the saline in advance, the effect of preventing the thrombus formation can also be improved.

Figure 8A:
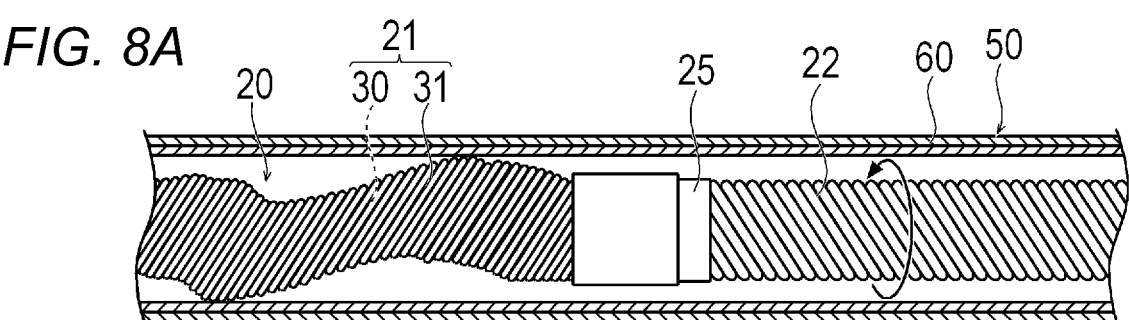
Figure 8B:
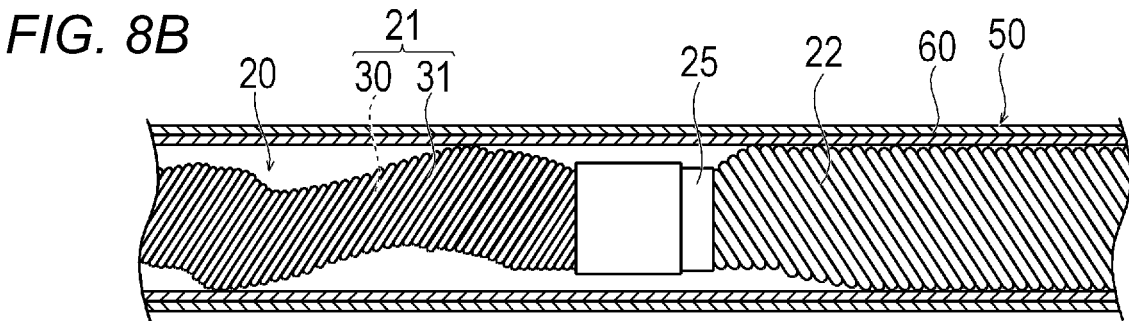

Excessive load torque may be applied to the drive shaft 20 rotating in the rated rotation direction, for example, in a case in which cutting resistance is excessive or in a case in which an inner peripheral surface of the outer tubular shaft 50 and the outer peripheral surface of the drive shaft 20 are in contact with each other when the outer tubular shaft 50 is largely bent. In this case, as shown in FIG. 8A, the first coil 30 of the distal coil 21 tends to expand in diameter, and the second coil 31 surrounding an outside of the first coil 30 tends to be reduced in diameter, so that a change in diameter of the distal coil 21 is relatively small. Therefore, when the distal coil 21 receives the excessive load torque, the distal coil 21 is twisted such that a coil center of the distal coil 21 draws a spiral inside the outer tubular shaft 50 while hardly changing the inner diameter and the outer diameter of the distal coil 21. In addition, since the wire rod of the distal coil 21 is thinner than the wire rod of the proximal coil 22, the distal coil 21 is more easily deformed than the proximal coil 22. Therefore, the distal coil 21 is deformed such that the coil center of the distal coil 21 is spirally twisted, and as a result, the distal coil 21 is more deformable (i.e., greatly deformed) in the radial direction than the proximal coil 22 and comes into contact with the outer tubular shaft 50. Accordingly, the distal coil 21 rather easily comes into contact with the inner peripheral surface of the outer tubular shaft 50 before the proximal coil 22 to generate braking torque. Therefore, a relatively long distance from the shaft joint portion 122 (see FIG. 2), which is the connection portion between the drive shaft 20 and the power shaft 121, to a position at which the braking torque is generated can be secured. Therefore, a load acting from the connection portion with the driving portion 120 to a contact position can be dispersed by the relatively long distance of the drive shaft 20. Further, when a contact point between the distal coil 21 and the outer tubular shaft 50 increases and the braking torque increases, the proximal coil 22 is deformed so as to loosen the spiral and expands in diameter, as shown in FIG. 8B. Accordingly, the proximal coil 22 is in contact with the inner peripheral surface of the outer tubular shaft 50, and the braking torque increases. Therefore, a position at which the braking torque acts gradually increases from the distal side toward the proximal side of the drive shaft 20, and thus the drive shaft 20 can be gently decelerated. Therefore, in the medical device 10, it is possible to prevent breakage of the shaft joint portion 122 on which a stress is likely to be concentrated.

In addition, the diameter of the proximal coil 22 also increases inside the power shaft 121, and the proximal coil 22 is in contact with the inner peripheral surface of the power shaft 121. Therefore, it is possible to prevent the breakage of the shaft joint portion 122 on which the stress is likely to be concentrated, which is a connection portion of the power shaft 121 and the proximal coil 22.

In addition, a portion of the proximal coil 22 between the most proximal end of the outer tubular shaft 50 and the most distal end of the power shaft 121 is covered with the proximal protection tube 28. Therefore, deformation in a radial direction is prevented in a range of the proximal coil 22 covered by the outer tubular shaft 50 and a range of the proximal coil 22 covered by the power shaft 121. On the other hand, since the portion of the proximal coil 22 between the most proximal end of the outer tubular shaft 50 and the most distal end of the power shaft 121 is covered with the proximal protection tube 28, the radial deformation due to the action of the load torque can be prevented.

After the cutting and the conveyance of the lesion area S are completed, the operator presses the switch 101. Accordingly, the rotation of the drive shaft 20 is stopped, and the liquid delivery performed by the liquid delivering portion 150 is stopped. Thereafter, the operator removes the medical device 10 from the blood vessel and completes the procedure.

As described above, the medical device 10 according to the present embodiment is the medical device 10 that removes the object in the body lumen. The medical device 10 includes: the rotatable drive shaft 20; the driving portion 120 configured to apply the torque to the proximal portion of the drive shaft 20 and having a specified rated rotation direction; the cutting portion 90 fixed to the distal portion of the drive shaft 20 and configured to cut the object; and the outer tubular shaft 50 rotatably accommodating the drive shaft 20, in which the drive shaft 20 includes the proximal coil 22 and the distal coil 21 disposed on the distal side with respect to the proximal coil 22, and the distal coil 21 is more greatly deformed in the radial direction than the proximal coil 22 by receiving the load torque while the drive shaft 20 is rotating in the rated rotation direction.

In the medical device 10 configured as described above, when the excessive load torque is applied to the drive shaft 20 rotating in the rated rotation direction, the distal coil 21 is more greatly deformed than the proximal coil 22, and relatively easily comes into contact with the inner peripheral surface of the outer tubular shaft 50 before the proximal coil 22 to generate the braking torque. Therefore, a long distance from the proximal portion of the drive shaft 20 that receives the torque from the driving portion 120 to the position at which the braking torque is generated can be secured. Therefore, the load acting from the connection portion with the driving portion 120 to the contact position can be dispersed by the long distance of the drive shaft 20. In addition, when the contact point between the distal coil 21 and the outer tubular shaft 50 increases and the braking torque increases, the deformation of the proximal coil 22 in the radial direction increases, and the proximal coil 22 comes into contact with the inner peripheral surface of the outer tubular shaft 50, thereby increasing the braking torque. Therefore, the position at which the braking torque acts gradually increases from the distal side toward the proximal side of the drive shaft 20, and thus the drive shaft 20 can be gently decelerated. Therefore, in the medical device 10, it is possible to prevent the breakage of the shaft joint portion 122 on which the stress is likely to be concentrated. Therefore, the medical device 10 reduces the stress concentration on a part of the drive shaft, and has stable rotation and durability.

In addition, the distal coil 21 is the multilayer coil that includes the first coil 30 including one or more wire rods and the second coil 31 including one or more wire rods and surrounding the first coil 30, the proximal coil 22 is the single-layer coil including one or more wire rods, the wire rod forming the first coil 30 is wound in the rated rotation direction toward the distal side when viewed from the proximal side, the wire rod forming the second coil 31 is wound in the direction opposite to the rated rotation direction toward the distal side as viewed from the proximal side, and the wire rod forming the proximal coil 22 is wound in the rated rotation direction toward the distal side when viewed from the proximal side. Accordingly, when the load torque is applied to the drive shaft 20 rotating in the rated rotation direction, the first coil 30 tends to expand in diameter, and the second coil 31 tends to reduce in diameter, so that the changes in the inner diameter and the outer diameter of the distal coil 21 can be reduced. Therefore, the distal coil 21 is deformed such that the coil center draws the spiral by receiving the load torque, and as a result, the distal coil 21 is more easily and greatly deformed in the radial direction than the proximal coil 22.

In addition, wire diameters of the wire rods forming the distal coil 21 are smaller than a wire diameter of the wire rod forming the proximal coil 22. Accordingly, the distal coil 21 is easily deformed in a larger degree than the proximal coil 22, and easily comes into contact with the inner peripheral surface of the outer tubular shaft 50.

In addition, the medical device 10 includes the conveying coil 23 which is sparsely wound to surround the distal coil 21, and the wire rod forming the conveying coil 23 is wound in the rated rotation direction toward the distal side when viewed from the proximal side. Accordingly, when the drive shaft 20 rotates in the rated rotation direction, the force toward the proximal side can be applied to the object or the liquid by the conveying coil 23.

In addition, the medical device 10 may include the conveying coil 23 that is sparsely wound to surround the distal coil 21, and the wire rod forming the conveying coil 23 may be wound in the direction opposite to the rated rotation direction toward the distal side when viewed from the proximal side. Accordingly, when the drive shaft 20 rotates in the rated rotation direction, the force toward the distal side can be applied to the object or the liquid by the conveying coil 23. In this case, the lumen in which the conveying coil 23 is disposed is preferably used for the liquid delivering.

Further, when the drive shaft 20 receives the load torque while rotating in the rated rotation direction, the distal coil 21 is twisted such that the coil center draws the spiral, and the proximal coil 22 is deformed so as to expand in diameter. Accordingly, the distal coil 21 is more easily and greatly deformed in the radial direction than the proximal coil 22.

In addition, when the drive shaft 20 receives the load torque while rotating in the rated rotation direction, the distal coil 21 is twisted such that the coil center of the distal coil 21 draws the spiral, and then the proximal coil 22 is deformed so as to expand in diameter. Accordingly, the distal coil 21 is more easily and greatly deformed in the radial direction than the proximal coil 22. Therefore, the distal coil 21 easily comes into contact with the inner peripheral surface of the outer tubular shaft 50 before the proximal coil 22 to generate the braking torque. Therefore, the position at which the braking torque acts increases from the distal side toward the proximal side of the drive shaft 20, and thus the drive shaft 20 can be gently decelerated. Therefore, in the medical device 10, it is possible to prevent the breakage of the shaft joint portion 122 on which the stress is likely to be concentrated.

In addition, the medical device 10 according to the present embodiment is the medical device 10 that removes the object in the body lumen. The medical device 10 includes: the rotatable drive shaft 20; the driving portion 120 configured to apply the torque to the proximal portion of the drive shaft 20; the cutting portion 90 fixed to the distal portion of the drive shaft 20 and configured to cut the object; and the outer tubular shaft 50 rotatably accommodating the drive shaft 20, in which the outer tubular shaft 50 includes the tubular inner layer 60 and the tubular outer layer 51 surrounding the inner layer 60, and the inner layer 60 includes the braided wire braided in the tubular shape or the coil wire wound in the spiral shape.

In the medical device 10 configured as described above, the inner layer 60 of the outer tubular shaft 50 disposed outside the drive shaft 20 is less likely to be deformed, and the inner diameter is easily maintained substantially constant even when the inner layer 60 is bent. Therefore, it is easy to set, to a desirable position, the position at which the braking torque is generated in the drive shaft 20 by the contact between the drive shaft 20 and the inner peripheral surface of the outer tubular shaft 50. Therefore, for example, in order to prevent the stress concentration on an interlock portion between the drive shaft 20 and the driving portion 120, it is easy to set the distal portion of the drive shaft 20 to come into contact with the inner peripheral surface of the outer tubular shaft 50 earlier than the proximal portion of drive shaft 20.

In addition, in the outer tubular shaft 50, the first lumen 54 through which the liquid flows is formed between the outer layer 51 and the inner layer 60. Accordingly, a function of the first lumen 54 as a flow path can be appropriately maintained by preventing the deformation of the inner layer 60. Therefore, an occurrence of a load on the outer tubular shaft 50 due to inhibition of the flow of the liquid passing through the first lumen 54 can be prevented.

In addition, the distal coil 21 includes the conveying coil 23 that is sparsely wound around the outermost layer 51, and the most distal end of the conveying coil 23 is located on the proximal side with respect to the most distal end of the inner layer 60. Accordingly, the conveying coil 23 forms the inner layer 60 on the proximal side with respect to the most distal end of the inner layer 60. Therefore, wear of the drive shaft 20 and the outer tubular shaft 50 can be reduced by disposing the inner layer 60 at a position in contact with the conveying coil 23.

In addition, the medical device 10 according to the present embodiment is the medical device 10 that removes the object in the body lumen. The medical device 10 includes: the rotatable drive shaft 20 including at least one coil; the driving portion 120 configured to apply the torque to the proximal portion of the drive shaft 20 and having the specified rated rotation direction; the cutting portion 90 fixed to the distal portion of the drive shaft 20 and configured to cut the object; and the outer tubular shaft 50 rotatably accommodating the drive shaft 20, in which the drive shaft 20 includes, at the proximal portion of the drive shaft 20, the proximal protection tube 28 covering the coil, and the proximal protection tube 28 is disposed at a position that is on the proximal side with respect to the outer tubular shaft 50 in a direction along an axial center of the outer tubular shaft 50 and overlaps with at least a part of the lumen (discharge lumen 136) having the inner diameter larger than the inner diameter of the outer tubular shaft 50, or at a position that overlaps with at least a part of the hole (discharge port 133) that penetrates with a direction component perpendicular to the axial center of the drive shaft 20.

In the medical device 10 configured as described above, the proximal protection tube 28 can prevent the coils of the drive shaft 20 disposed at positions overlapping the lumen or the hole from being deformed by receiving the load torque and entering the lumen or the hole wider than the inner diameter of the outer tubular shaft 50. Therefore, the medical device 10 prevents breakage of the drive shaft 20, and has stable rotation and durability.

It is noted that this disclosure is not limited to the embodiments described above, and various modifications can be made by those skilled in the art within a scope of the technical idea of this disclosure. For example, the body lumen into which the medical device 10 is inserted is not limited to the blood vessel, and may be, for example, a vessel, a urinary duct, a bile duct, a fallopian tube, or a hepatic duct.

Figure 9A:
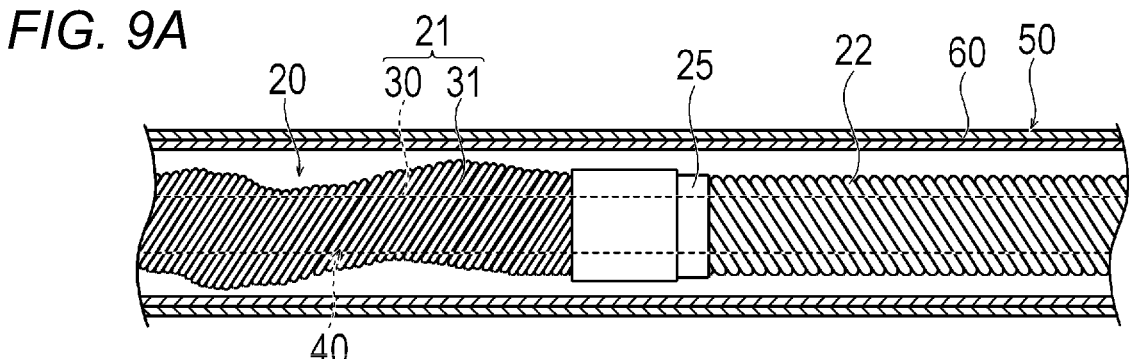
Figure 9B:
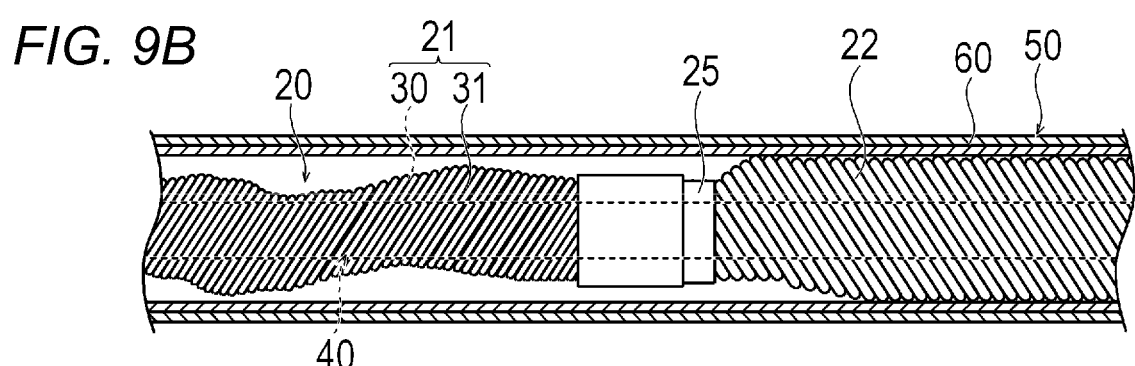

In addition, as in a first modification in FIG. 9A, the distal coil 21 that is more greatly deformed in the radial direction than the proximal coil 22 may come into contact with an outer peripheral surface of the inner guide wire lumen tube 40 instead of the outer tubular shaft 50 on an outer side to generate braking torque. When a contact point between the distal coil 21 and the guide wire lumen tube 40 increases and the braking torque increases, the proximal coil 22 expands in diameter and comes into contact with the inner peripheral surface of the outer tubular shaft 50, as shown in FIG. 9B. Accordingly, the position at which the braking torque acts gradually increases from the distal side toward the proximal side of the drive shaft 20, and the drive shaft 20 can be gently decelerated.

Figure 10A:
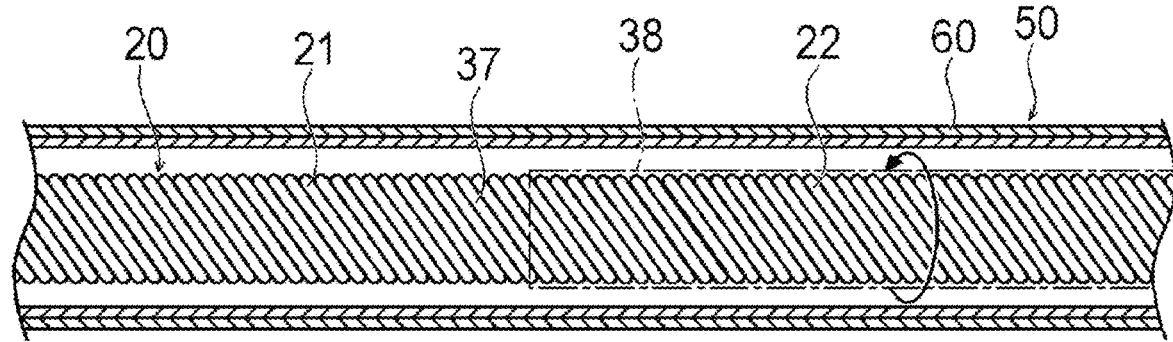
Figure 10B:
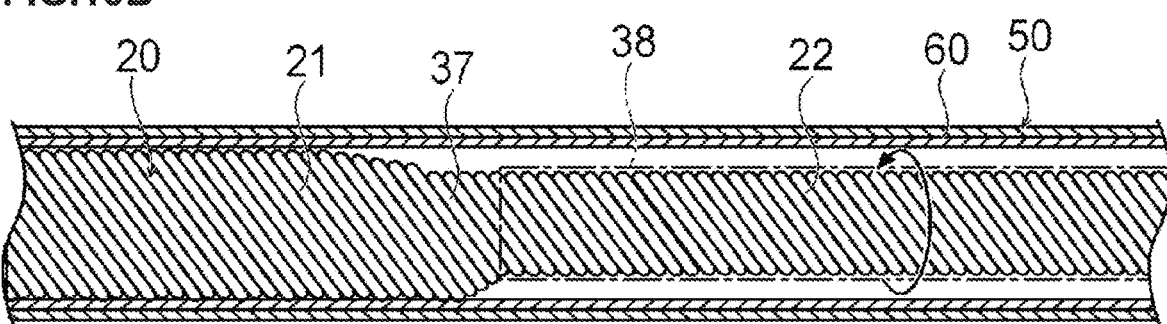

In addition, a configuration is not particularly limited as long as the distal side of the drive shaft 20 can be more greatly deformed in the radial direction than the proximal side by applying the load torque. For example, as in a second modification in FIG. 10A, the distal coil 21 and the proximal coil 22 may include a common coil 37 formed of a common wire rod wound in the rated rotation direction toward the distal side when viewed from the proximal side, and the proximal coil 22 may include a reinforcement tube 38 covering an outer peripheral surface of the common coil 37. The reinforcement tube 38 is a tubular body that can expand and contract in a radial direction. The reinforcement tube 38 is formed of, for example, a heat-shrinkable tube. Accordingly, since the deformation of the proximal coil 22 is prevented by the reinforcement tube 38, the distal coil 21 is easily deformed so as to have a larger diameter than the proximal coil 22. Therefore, as shown in FIG. 10B, the distal coil 21 is easily brought into contact with the outer tubular shaft 50 before the proximal coil 22. When a contact point between the distal coil 21 and the outer tubular shaft 50 increases and braking torque increases, the distal coil 21 expands in diameter or is deformed such that the coil center is twisted in a spiral shape, and can be brought into contact with the inner peripheral surface of the outer tubular shaft 50.

Figure 11A:
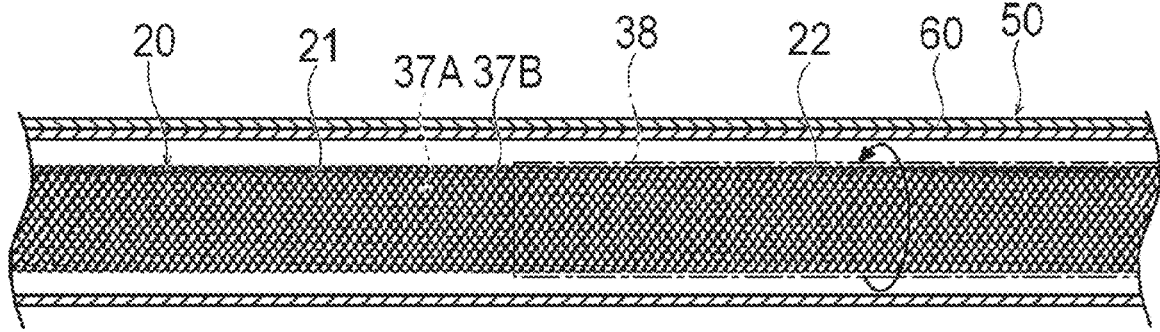
Figure 11B:
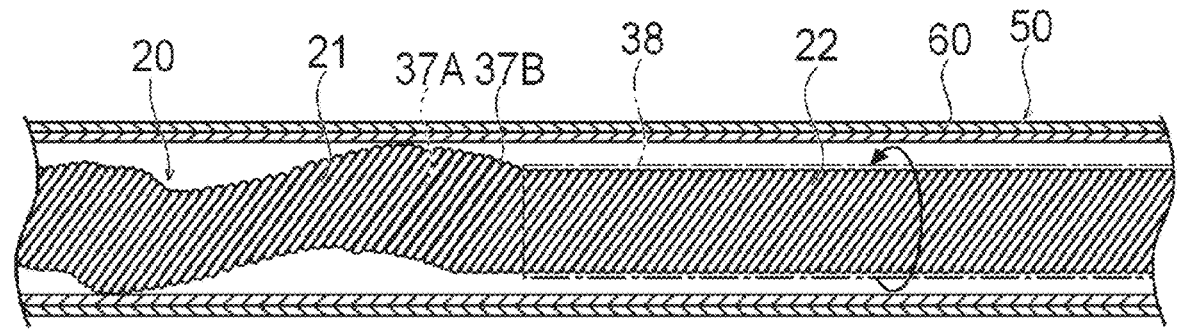

In addition, as in a third modification shown in FIG. 11A, the distal coil 21 and the proximal coil 22 may include a first common coil 37A formed of a common wire rod wound in the rated rotation direction toward the distal side when viewed from the proximal side, and a second common coil 37B formed of a common wire rod wound in the direction opposite to the rated rotation direction toward the distal side when viewed from the proximal side, and the proximal coil 22 may include the reinforcement tube 38 covering an outer peripheral surface of the second common coil 37B. Accordingly, since the deformation of the proximal coil 22 is prevented by the reinforcement tube 38, the distal coil 21 is easily deformed in a larger degree than the proximal coil 22 as shown in FIG. 11B. Therefore, the distal coil 21 is easily brought into contact with the outer tubular shaft 50 before the proximal coil 22. When a contact point between the distal coil 21 and the outer tubular shaft 50 increases and braking torque increases, the proximal coil 22 expands in diameter or is deformed such that the coil center is twisted in a spiral shape, and can be brought into contact with the inner peripheral surface of the outer tubular shaft 50.

Figures 12A, 12B, 13A, 13B:
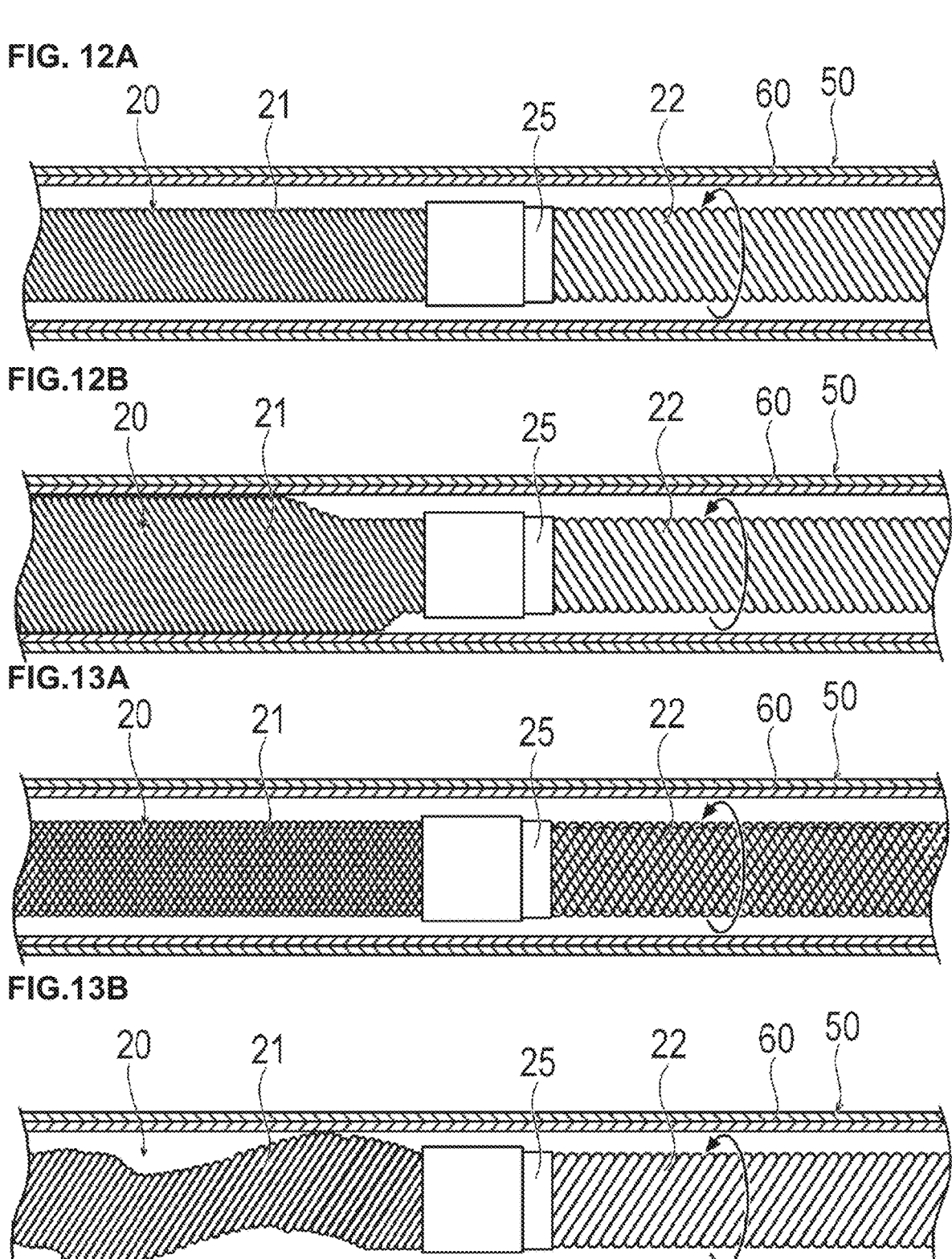

In addition, as in a fourth modification shown in FIG. 12A, each of the distal coil 21 and the proximal coil 22 may be a single-layer coil formed of a wire rod wound in the rated rotation direction toward the distal side when viewed from the proximal side. Further, the wire rod of the distal coil 21 is thinner than the wire rod of the proximal coil 22. Accordingly, the distal coil 21 is easily deformed so as to have a larger diameter than the proximal coil 22. Therefore, as shown in FIG. 12B, the distal coil 21 easily expands in diameter before the proximal coil 22 to come into contact with the outer tubular shaft 50. When a contact point between the distal coil 21 and the outer tubular shaft 50 increases and braking torque increases, the proximal coil 22 expands in diameter and comes into contact with the inner peripheral surface of the outer tubular shaft 50.

In addition, as in a fifth modification shown in FIG. 13A, each of the distal coil 21 and the proximal coil 22 may be a multilayer coil formed of a wire rod wound in the direction opposite to the rated rotation direction toward the distal side when viewed from the proximal side. Further, the wire rod of the distal coil 21 is thinner than the wire rod of the proximal coil 22. Accordingly, the distal coil 21 is easily deformed so as to have a larger diameter than the proximal coil 22. Therefore, as shown in FIG. 13B, the distal coil 21 is easily deformed such that the coil center is twisted in a spiral shape before the proximal coil 22 to come into contact with the outer tubular shaft 50. When a contact point between the distal coil 21 and the outer tubular shaft 50 increases and braking torque increases, the distal coil 21 is deformed such that the coil center of the distal coil 21 is twisted in a spiral shape, and can be brought into contact with the inner peripheral surface of the outer tubular shaft 50.

In addition, the distal coil 21 and the proximal coil 22 become harder and less deformable as the number (the number of threads) of wire rods forming each layer increases. Therefore, the distal coil 21 may be more easily deformed than the proximal coil 22 by adjusting the number of threads.

The detailed description above describes embodiments of a medical device for removing an object in a body lumen. These disclosed embodiments represent examples of the medical device for removing an object in a body lumen disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device configured to remove an object in a body lumen, the medical device comprising:
   a rotatable drive shaft;
   a motor configured to apply torque to a proximal portion of the drive shaft and having a specified rated rotation direction;
   a cutting portion fixed to a distal portion of the drive shaft and configured to cut the object, the cutting portion being a member with abrasive grains or a sharp blade;
   an outer tubular shaft configured to rotatably accommodate the drive shaft; and
   the drive shaft includes a proximal coil, a distal coil, and a tubular interlock arranged between the proximal coil and the distal coil, the tubular interlock interlocking the proximal coil to the distal coil, the distal coil being disposed on a distal side of the proximal coil, and wherein the distal coil is more deformable in a radial direction than the proximal coil by receiving load torque while the drive shaft is rotating in the rated rotation direction.

2. The medical device according to claim 1, wherein the distal coil is a multilayer coil that includes a first coil including one or more wire rods and a second coil including one or more wire rods, the second coil surrounding the first coil;
   the proximal coil is a single-layer coil including one or more wire rods;
   the one or more wire rods forming the first coil are wound in the rated rotation direction toward the distal side when viewed from a proximal side;

the one or more wire rods forming the second coil are wound in a direction opposite to the rated rotation direction toward the distal side when viewed from the proximal side; and
   the one or more wire rods forming the proximal coil are wound in the rated rotation direction toward the distal side when viewed from the proximal side.

3. The medical device according to claim 1, wherein a wire diameter of a wire rod forming the distal coil is smaller than a wire diameter of a wire rod forming the proximal coil.

4. The medical device according to claim 1, further comprising:
   a conveying coil wound around the distal coil, the conveying coil having a gap or spacing between windings of the conveying coil; and
   wherein a wire rod forming the conveying coil is wound in the rated rotation direction toward the distal side when viewed from a proximal side.

5. The medical device according to claim 1, further comprising:
   a conveying coil wound to surround the distal coil, the conveying coil having a gap or spacing between windings of the conveying coil; and
   wherein a wire rod forming the conveying coil is wound in a direction opposite to the rated rotation direction toward the distal side when viewed from a proximal side.

6. The medical device according to claim 1, wherein when the drive shaft receives the load torque while rotating in the rated rotation direction, the distal coil is wound in a direction of the rated rotation direction such that a coil center draws a spiral and is tightened, and the proximal coil is wound in a direction opposite of the rated rotation direction and is deformed so as to expand in diameter.

7. The medical device according to claim 6, wherein when the drive shaft receives the load torque while rotating in the rated rotation direction, the distal coil is first twisted such that the coil center draws the spiral, and then the proximal coil is deformed so as to expand in diameter.

8. The medical device according to claim 1, wherein the rated rotation direction is a rotational direction of the drive shaft when the medical device is being used for cutting of the object in the body lumen with the cutting portion and a conveyance of the cut object in the body lumen to a distal side of the medical device.

9. The medical device according to claim 1, wherein the outer tubular shaft includes a tubular inner layer and a tubular outer layer surrounding the tubular inner layer.

10. The medical device according to claim 9, wherein the inner layer includes a braided wire braided in a tubular shape.

11. The medical device according to claim 9, wherein the inner layer includes a coil wire wound in a spiral shape.

12. A medical device configured to remove an object in a body lumen, the medical device comprising:
   a rotatable drive shaft, the drive shaft includes a proximal coil, a distal coil, and a tubular interlock arranged between the proximal coil and the distal coil, the tubular interlock interlocking the proximal coil to the distal coil, the distal coil being disposed on a distal side of the proximal coil, and wherein the distal coil is more deformable in a radial direction than the proximal coil by receiving load torque while the drive shaft is rotating in the rated rotation direction;
   a motor configured to apply torque to a proximal portion of the drive shaft;

a cutting portion fixed to a distal portion of the drive shaft and configured to cut the object, the cutting portion being a member with abrasive grains or a sharp blade;

an outer tubular shaft configured to rotatably accommodate the drive shaft;

the outer tubular shaft includes a tubular inner layer and a tubular outer layer surrounding the tubular inner layer; and the inner layer includes a braided wire braided in a tubular shape or a coil wire wound in a spiral shape.

13. The medical device according to claim 12, further comprising:

a first lumen through which a liquid flows is formed between the outer layer and the inner layer of the outer tubular shaft.

14. The medical device according to claim 12, further comprising:

a conveying coil wound to surround a distal coil of the drive shaft, the conveying coil having a gap or spacing between windings of the conveying coil; and wherein the most distal end of the conveying coil is located on a proximal side with respect to the most distal end of the inner layer.

15. The medical device according to claim 12, wherein the distal coil is a multilayer coil that includes a first coil including one or more wire rods and a second coil including one or more wire rods, the second coil surrounding the first coil;

the proximal coil is a single-layer coil including one or more wire rods;

the one or more wire rods forming the first coil are wound in the rated rotation direction toward the distal side when viewed from a proximal side;

the one or more wire rods forming the second coil are wound in a direction opposite to the rated rotation direction toward the distal side when viewed from the proximal side; and the one or more wire rods forming the proximal coil are wound in the rated rotation direction toward the distal side when viewed from the proximal side.

16. A medical device configured to remove an object in a body lumen, the medical device comprising:

a rotatable drive shaft, the drive shaft includes a proximal coil, a distal coil, and a tubular interlock arranged between the proximal coil and the distal coil, the tubular interlock interlocking the proximal coil to the distal coil, the distal coil being disposed on a distal side of the proximal coil, and wherein the distal coil is more deformable in a radial direction than the proximal coil by receiving load torque while the drive shaft is rotating in the rated rotation direction;

a motor configured to apply torque to a proximal portion of the drive shaft and having a specified rated rotation direction;

a cutting portion fixed to a distal portion of the drive shaft and configured to cut the object, the cutting portion being a member with abrasive grains or a sharp blade;

an outer tubular shaft configured to rotatably accommodate the drive shaft;

the drive shaft includes a proximal protection tube covering the coil at the proximal portion of the drive shaft; and wherein the proximal protection tube is disposed at a position that is on a proximal side with respect to the outer tubular shaft in a direction along an axial center of the outer tubular shaft and overlaps with at least a part of a lumen having an inner diameter larger than an inner diameter of the outer tubular shaft, or at a position that overlaps with at least a part of a hole that penetrates with a direction component perpendicular to an axial center of the drive shaft.

17. The medical device according to claim 1, wherein the tubular interlock includes a tubular distal fixing portion that fixes a proximal end portion of the wire rods constituting the distal coil, and a tubular proximal fixing portion that fixes a distal end portion of the wire rod constituting the proximal coil.

18. The medical device according to claim 17, further comprising:

a strain relief member fixed to the tubular interlock, the strain relief member being a rigid circular tube that covers the tubular interlock and extend distally of a distal end of the tubular interlock.

19. The medical device according to claim 18, wherein an inner diameter of the strain relief member is larger than an outer diameter of the distal coil such that the distal coil can be bent inside the strain relief member.

* * * * *